(12) United States Patent
Kavinaugh et al.

(10) Patent No.: US 7,699,884 B2
(45) Date of Patent: Apr. 20, 2010

(54) METHOD OF STENTING WITH MINIMAL DIAMETER GUIDED DELIVERY SYSTEMS

(75) Inventors: Joe Kavinaugh, Mountain View, CA (US); Frank Becking, Palo Alto, CA (US); William R. George, Santa Cruz, CA (US); Julian Nikolchev, Portola Valley, CA (US)

(73) Assignee: Cardiomind, Inc., Sunnyvale, CA (US)

( * ) Notice: Subject to any disclaimer, the term of this patent is extended or adjusted under 35 U.S.C. 154(b) by 723 days.

(21) Appl. No.: 11/388,217

(22) Filed: Mar. 22, 2006

(65) Prior Publication Data

US 2007/0225789 A1 Sep. 27, 2007

(51) Int. Cl.
*A61F 2/06* (2006.01)

(52) U.S. Cl. .................................... 623/1.12

(58) Field of Classification Search ............... 623/1.11, 623/1.12, 1.13, 1.35, 2.11; 606/108, 194; 604/103.04
See application file for complete search history.

(56) References Cited

U.S. PATENT DOCUMENTS

| | | | |
|---|---|---|---|
| 4,503,569 A | 3/1985 | Dotter | |
| 4,512,338 A | 4/1985 | Balko et al. | |
| 4,553,545 A | 11/1985 | Maass et al. | |
| 4,562,596 A | 1/1986 | Kornberg | |
| 4,580,568 A | 4/1986 | Gianturco | |
| 4,655,771 A | 4/1987 | Wallsten | |
| 4,665,918 A | 5/1987 | Garza et al. | |
| 4,732,152 A | 3/1988 | Wallsten et al. | |
| 4,733,665 A | 3/1988 | Palmaz | |
| 4,762,128 A | 8/1988 | Rosenbluth | |
| 4,768,507 A | 9/1988 | Fischell et al. | |
| 4,771,773 A | 9/1988 | Kropf | |
| 4,776,337 A | 10/1988 | Palmaz | |
| 4,830,003 A | 5/1989 | Wolff et al. | |
| 4,875,480 A | 10/1989 | Imbert | |
| 4,878,906 A | 11/1989 | Lindemann et al. | |
| 4,913,141 A | 4/1990 | Hillstead | |
| 4,954,126 A | 9/1990 | Wallsten | |
| 4,969,890 A | 11/1990 | Sugita et al. | |
| 4,998,539 A | 3/1991 | Delsanti | |
| 5,019,085 A | 5/1991 | Hillstead | |
| 5,019,090 A | 5/1991 | Pinchuk | |
| 5,026,377 A | 6/1991 | Burton et al. | |
| 5,035,706 A | 7/1991 | Giantureo et al. | |

(Continued)

FOREIGN PATENT DOCUMENTS

WO    WO 2004/087006 A2    10/2004

OTHER PUBLICATIONS

Duerig et al., "An overview of superelastic stent desing" Min Invas Ther & Allied Technol, 9(3/4):234-246 (2000).

(Continued)

*Primary Examiner*—Anhtuan T Nguyen
*Assistant Examiner*—Elizabeth Houston
(74) *Attorney, Agent, or Firm*—Townsend and Townsend and Crew LLP

(57) ABSTRACT

Medical devices and methods for delivery or implantation of prostheses within hollow body organs and vessels or other luminal anatomy are disclosed. The subject technologies may be used in the treatment of atherosclerosis in stenting procedures or be used in a variety of other procedures.

13 Claims, 15 Drawing Sheets

U.S. PATENT DOCUMENTS

| | | | |
|---|---|---|---|
| 5,061,275 A | 10/1991 | Wallsten et al. | |
| 5,064,435 A | 11/1991 | Porter | |
| 5,067,957 A | 11/1991 | Jervis | |
| 5,071,407 A | 12/1991 | Termin et al. | |
| 5,089,006 A | 2/1992 | Stiles | |
| 5,102,417 A | 4/1992 | Palmaz | |
| 5,147,370 A | 9/1992 | McNamara et al. | |
| 5,158,548 A | 10/1992 | Lau et al. | |
| 5,201,757 A | 4/1993 | Heyn et al. | |
| 5,221,261 A | 6/1993 | Termin et al. | |
| 5,242,399 A | 9/1993 | Lau et al. | |
| 5,242,452 A | 9/1993 | Inoue | |
| 5,246,445 A | 9/1993 | Yachia et al. | |
| 5,263,964 A | 11/1993 | Purdy | |
| 5,266,073 A | 11/1993 | Wall | |
| 5,290,305 A | 3/1994 | Inoue | |
| 5,306,294 A | 4/1994 | Winston et al. | |
| 5,354,295 A | 10/1994 | Guglielmi et al. | |
| 5,360,401 A | 11/1994 | Turnland et al. | |
| 5,372,600 A | 12/1994 | Beyar et al. | |
| 5,407,432 A | 4/1995 | Solar | |
| 5,409,019 A * | 4/1995 | Wilk | 128/898 |
| 5,413,559 A * | 5/1995 | Sirhan et al. | 604/103.04 |
| 5,415,664 A | 5/1995 | Pinchuk | |
| 5,433,723 A | 7/1995 | Lindenberg et al. | |
| 5,445,646 A | 8/1995 | Euteneuer et al. | |
| 5,476,505 A | 12/1995 | Limon | |
| 5,484,444 A | 1/1996 | Braunschweiler et al. | |
| 5,507,771 A | 4/1996 | Gianturco | |
| 5,522,836 A | 6/1996 | Palermo | |
| 5,522,883 A | 6/1996 | Slater et al. | |
| 5,534,007 A | 7/1996 | St. Germain et al. | |
| 5,540,680 A | 7/1996 | Guglielmi et al. | |
| 5,554,181 A | 9/1996 | Das | |
| 5,569,245 A | 10/1996 | Guglielmi et al. | |
| 5,571,135 A | 11/1996 | Fraser et al. | |
| 5,634,928 A * | 6/1997 | Fischell et al. | 623/1.11 |
| 5,643,254 A | 7/1997 | Scheldrup et al. | |
| 5,690,644 A | 11/1997 | Yurek et al. | |
| 5,702,418 A | 12/1997 | Ravenscroft | |
| 5,733,325 A | 3/1998 | Robinson et al. | |
| 5,772,669 A | 6/1998 | Vrba | |
| 5,776,142 A | 7/1998 | Gunderson | |
| 5,782,838 A | 7/1998 | Beyar et al. | |
| 5,788,707 A | 8/1998 | Del Toro et al. | |
| 5,797,952 A | 8/1998 | Klein | |
| 5,800,517 A | 9/1998 | Anderson et al. | |
| 5,817,101 A | 10/1998 | Fiedler | |
| 5,824,041 A | 10/1998 | Lenker et al. | |
| RE35,988 E | 12/1998 | Winston et al. | |
| 5,843,090 A | 12/1998 | Schuetz | |
| 5,851,206 A | 12/1998 | Guglielmi et al. | |
| 5,855,578 A | 1/1999 | Guglielmi et al. | |
| 5,873,907 A | 2/1999 | Frantzen | |
| 5,919,187 A | 7/1999 | Guglielmi et al. | |
| 5,919,204 A | 7/1999 | Lukic et al. | |
| 5,957,930 A | 9/1999 | Vrba | |
| 5,968,052 A | 10/1999 | Sullivan et al. | |
| 5,980,514 A | 11/1999 | Kupiecki et al. | |
| 5,984,929 A | 11/1999 | Bashiri et al. | |
| 5,989,280 A | 11/1999 | Euteneuer et al. | |
| 6,019,779 A | 2/2000 | Thorud et al. | |
| 6,027,516 A | 2/2000 | Kolobow et al. | |
| 6,042,588 A | 3/2000 | Munsinger et al. | |
| 6,056,759 A | 5/2000 | Fiedler | |
| 6,059,779 A | 5/2000 | Mills | |
| 6,059,813 A | 5/2000 | Vrba et al. | |
| 6,063,101 A | 5/2000 | Jacobsen et al. | |
| 6,071,286 A | 6/2000 | Mawad | |
| 6,077,297 A | 6/2000 | Robinson et al. | |
| 6,093,194 A | 7/2000 | Mikus et al. | |
| 6,096,045 A | 8/2000 | Del Toro et al. | |
| 6,102,942 A | 8/2000 | Ahari | |
| 6,113,608 A | 9/2000 | Monroe et al. | |
| 6,117,140 A | 9/2000 | Munsinger | |
| 6,120,522 A | 9/2000 | Vrba et al. | |
| 6,123,720 A | 9/2000 | Anderson et al. | |
| 6,126,685 A | 10/2000 | Lenker et al. | |
| 6,139,524 A | 10/2000 | Killion | |
| 6,139,564 A | 10/2000 | Teoh | |
| 6,156,061 A | 12/2000 | Wallace et al. | |
| 6,165,178 A | 12/2000 | Bashiri et al. | |
| 6,168,529 B1 | 1/2001 | Moulinet | |
| 6,168,616 B1 | 1/2001 | Brown, III | |
| 6,168,618 B1 | 1/2001 | Frantzen | |
| 6,174,327 B1 | 1/2001 | Mertens et al. | |
| 6,183,481 B1 | 2/2001 | Lee et al. | |
| 6,206,888 B1 | 3/2001 | Bicek et al. | |
| 6,214,036 B1 | 4/2001 | Letendre et al. | |
| 6,221,081 B1 | 4/2001 | Mikus et al. | |
| 6,228,110 B1 | 5/2001 | Munsinger | |
| 6,231,564 B1 * | 5/2001 | Gambale | 604/528 |
| 6,238,430 B1 | 5/2001 | Klumb et al. | |
| 6,245,097 B1 | 6/2001 | Inoue | |
| 6,248,122 B1 | 6/2001 | Klumb et al. | |
| 6,254,609 B1 | 7/2001 | Vrba et al. | |
| 6,254,611 B1 | 7/2001 | Vrba | |
| 6,254,628 B1 | 7/2001 | Wallace et al. | |
| 6,267,783 B1 | 7/2001 | Letendre et al. | |
| 6,280,465 B1 | 8/2001 | Cryer | |
| 6,287,331 B1 | 9/2001 | Heath | |
| 6,302,893 B1 | 10/2001 | Limon et al. | |
| 6,306,141 B1 | 10/2001 | Jervis | |
| 6,342,066 B1 | 1/2002 | Toro et al. | |
| 6,350,278 B1 | 2/2002 | Lenker et al. | |
| 6,375,660 B1 | 4/2002 | Fischell et al. | |
| 6,380,457 B1 | 4/2002 | Yurek et al. | |
| 6,391,050 B1 | 5/2002 | Broome | |
| 6,391,051 B2 | 5/2002 | Sullivan, III et al. | |
| 6,395,017 B1 | 5/2002 | Dwyer et al. | |
| 6,409,752 B1 | 6/2002 | Boatman et al. | |
| 6,413,269 B1 | 7/2002 | Bui et al. | |
| 6,416,536 B1 | 7/2002 | Yee | |
| 6,416,545 B1 | 7/2002 | Mikus et al. | |
| 6,425,914 B1 | 7/2002 | Wallace et al. | |
| 6,425,915 B1 | 7/2002 | Khosravi et al. | |
| 6,428,489 B1 | 8/2002 | Jacobsen et al. | |
| 6,451,025 B1 | 9/2002 | Jervis | |
| 6,458,092 B1 | 10/2002 | Gambale et al. | |
| 6,468,266 B1 | 10/2002 | Bashiri et al. | |
| 6,468,298 B1 | 10/2002 | Pelton | |
| 6,468,301 B1 | 10/2002 | Amplatz et al. | |
| 6,482,227 B1 | 11/2002 | Solovay | |
| 6,488,700 B2 | 12/2002 | Klumb et al. | |
| 6,517,569 B2 | 2/2003 | Mikus et al. | |
| 6,530,947 B1 | 3/2003 | Euteneuer et al. | |
| 6,533,805 B1 | 3/2003 | Jervis | |
| 6,537,295 B2 | 3/2003 | Petersen | |
| 6,562,063 B1 | 5/2003 | Euteneuer et al. | |
| 6,562,064 B1 | 5/2003 | deBeer | |
| 6,579,297 B2 | 6/2003 | Bicek et al. | |
| 6,579,308 B1 | 6/2003 | Jansen et al. | |
| 6,582,460 B1 | 6/2003 | Cryer | |
| 6,607,539 B1 | 8/2003 | Hayashi et al. | |
| 6,607,551 B1 | 8/2003 | Sullivan et al. | |
| 6,620,152 B2 | 9/2003 | Guglielmi | |
| 6,623,518 B2 | 9/2003 | Thompson et al. | |
| 6,629,981 B2 | 10/2003 | Bui et al. | |
| 6,645,237 B2 | 11/2003 | Klumb et al. | |
| 6,656,212 B2 | 12/2003 | Ravenscroft et al. | |
| 6,660,031 B2 | 12/2003 | Tran et al. | |
| 6,660,032 B2 | 12/2003 | Klumb et al. | |
| 6,666,881 B1 | 12/2003 | Richter et al. | |
| 6,669,719 B2 | 12/2003 | Wallace et al. | |

| | | |
|---|---|---|
| 6,676,666 B2 | 1/2004 | Vrba et al. |
| 6,692,521 B2 | 2/2004 | Pinchasik |
| 6,709,425 B2 | 3/2004 | Gambale et al. |
| 6,716,238 B2 | 4/2004 | Elliott |
| 6,736,839 B2 | 5/2004 | Cummings |
| 6,802,858 B2 | 10/2004 | Gambale et al. |
| 6,814,746 B2 | 11/2004 | Thompson et al. |
| 6,833,003 B2 * | 12/2004 | Jones et al. ............ 623/1.11 |
| 6,843,802 B1 | 1/2005 | Villalobos et al. |
| 6,860,899 B1 | 3/2005 | Rivelli, Jr. |
| 6,936,065 B2 | 8/2005 | Khan et al. |
| 6,989,024 B2 | 1/2006 | Hebert et al. |
| 7,011,673 B2 | 3/2006 | Fischell et al. |
| 2001/0049547 A1 | 12/2001 | Moore |
| 2002/0120323 A1 | 8/2002 | Thompson et al. |

OTHER PUBLICATIONS

Kandzari et al., "Clinical and Angiographic Efficacy of a Self-Expanding Nitinol Stent in Saphenous Vein Graft Athersclerotic Disease" Am. Heart J 145(5):868-874 (2003).

Rieu et al., "Radical Force of Coronary Stents: A Comparative Analysis" Catherization and Cardiovascular Interventions 46:380-391 (1999).

Schuessler et al., Stent Materials and Manufacturing: Requirements and Possibilities/Opportunities, ASM Materials & Processes, Anaheim, CA (Sep. 8-10, 2003).

Stoeckel et al., "A Survey of Stent Desings" Min Invas Ther & Allied Technol 11(4):137-147 (2002).

Welt et al., "Coronary Artery Stents: Design and Biologic Considerations" Cardiology Special Edition 9(2) 9-14 (2003).

Rogers, C, "DES Overview: Agents: release mechanism and stent platform".

* cited by examiner

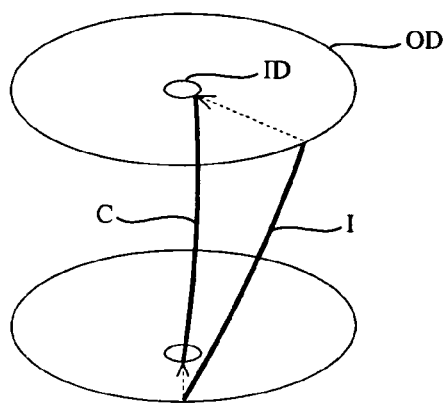
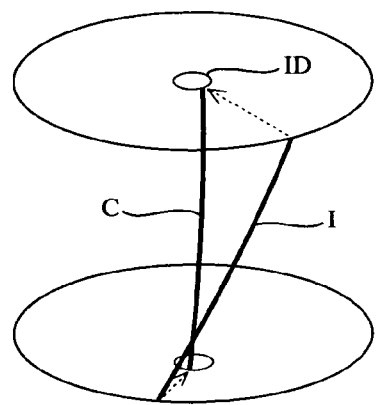
Fig. 3A          Fig. 3B
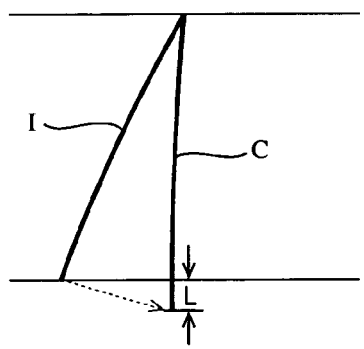
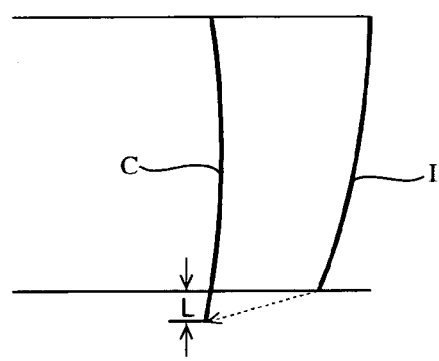
Fig. 3C          Fig. 3D
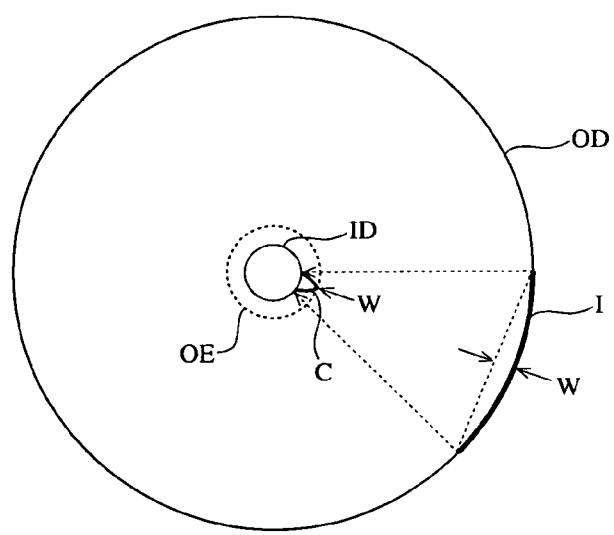
Fig. 3E

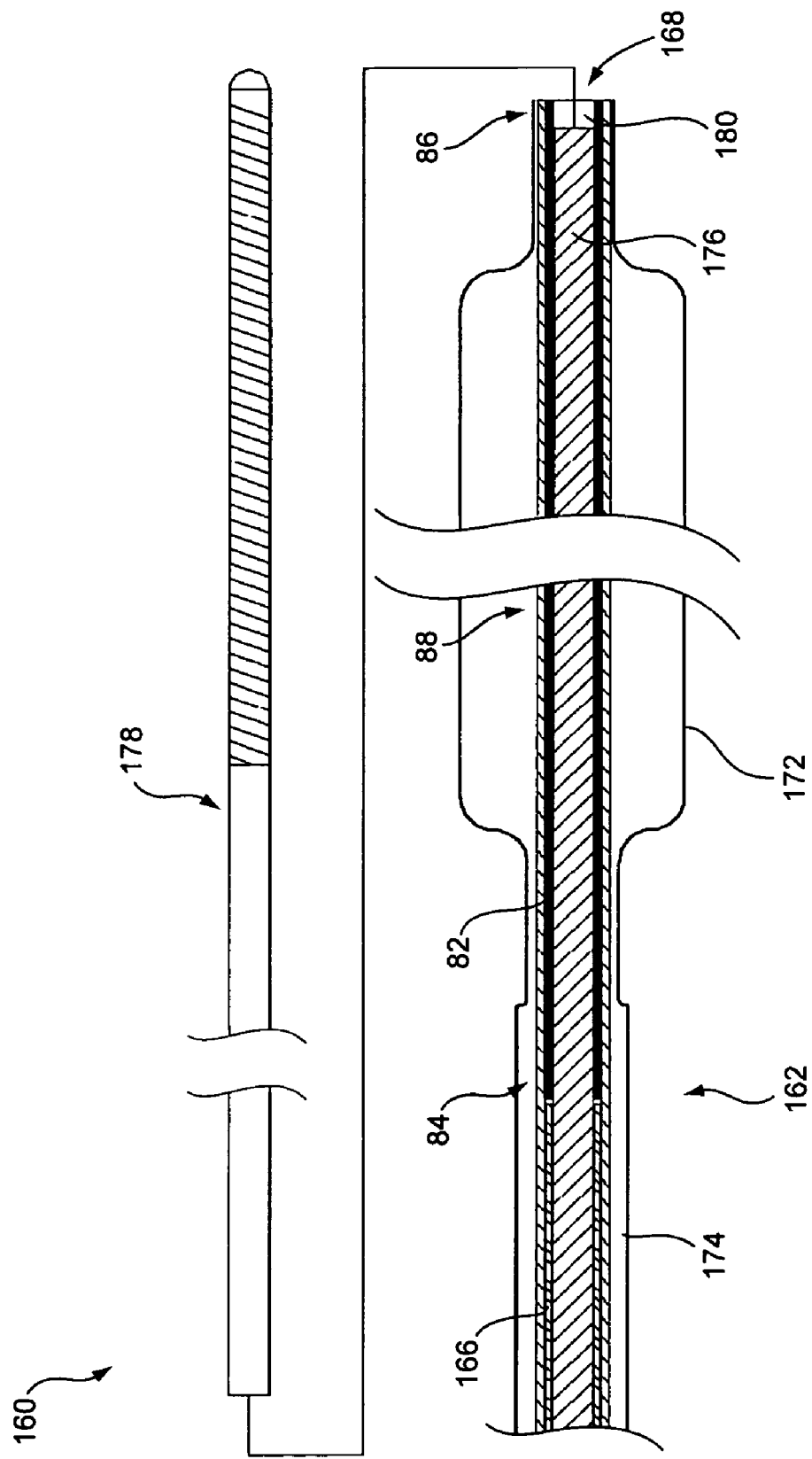

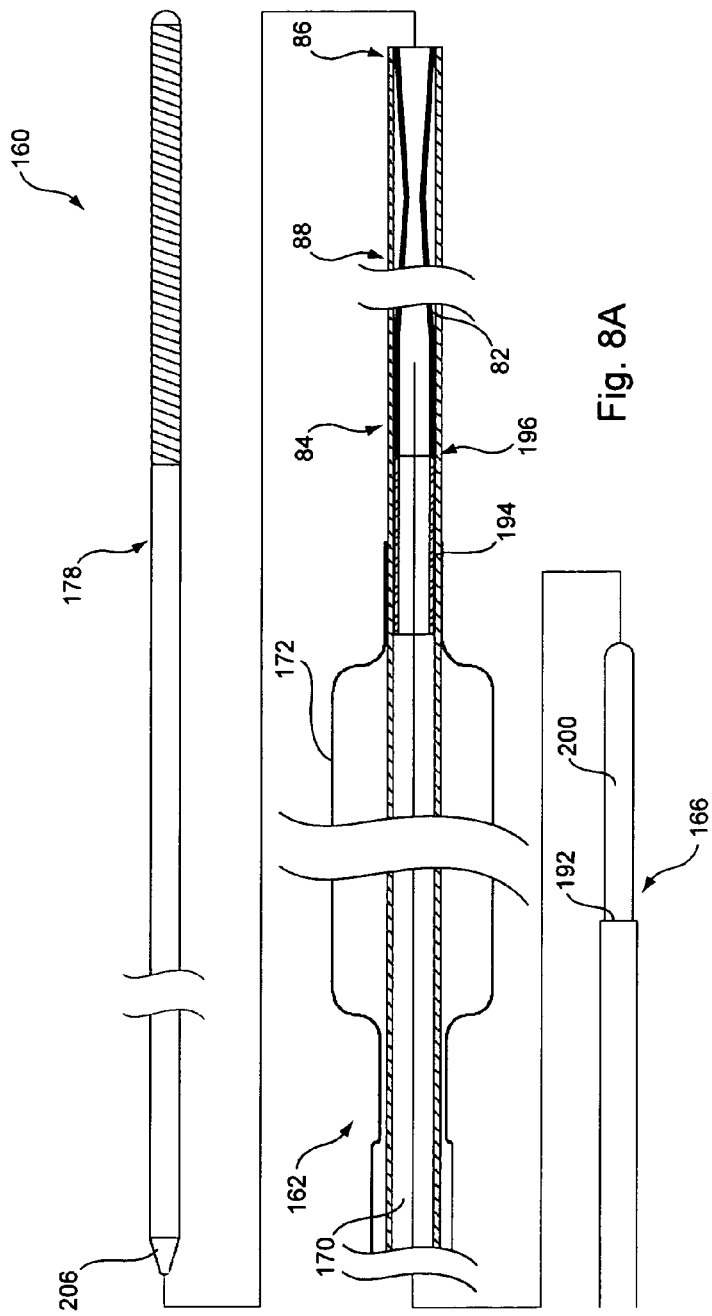
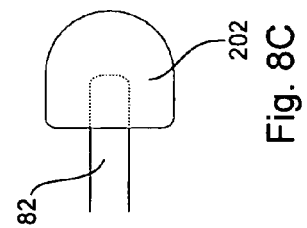
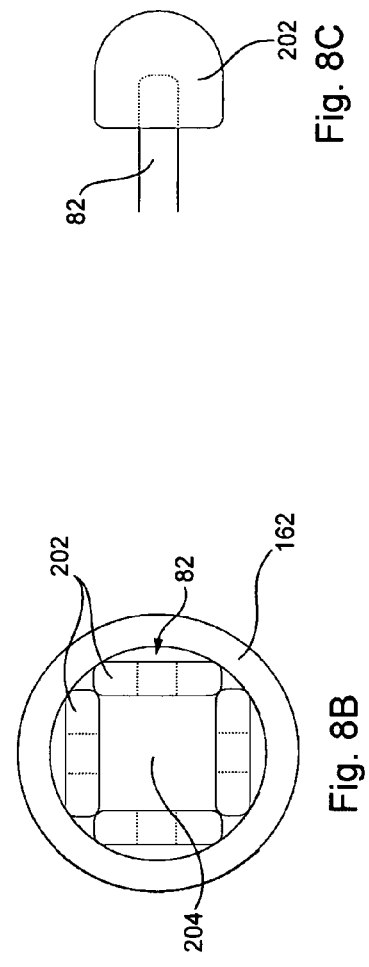

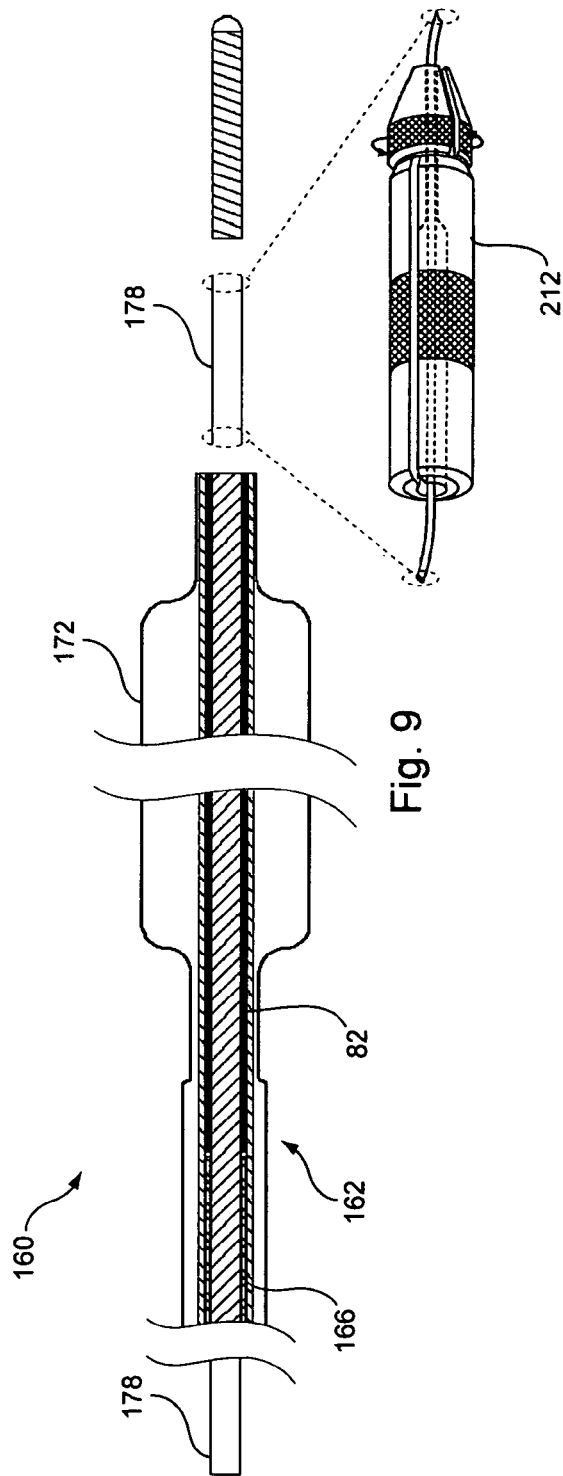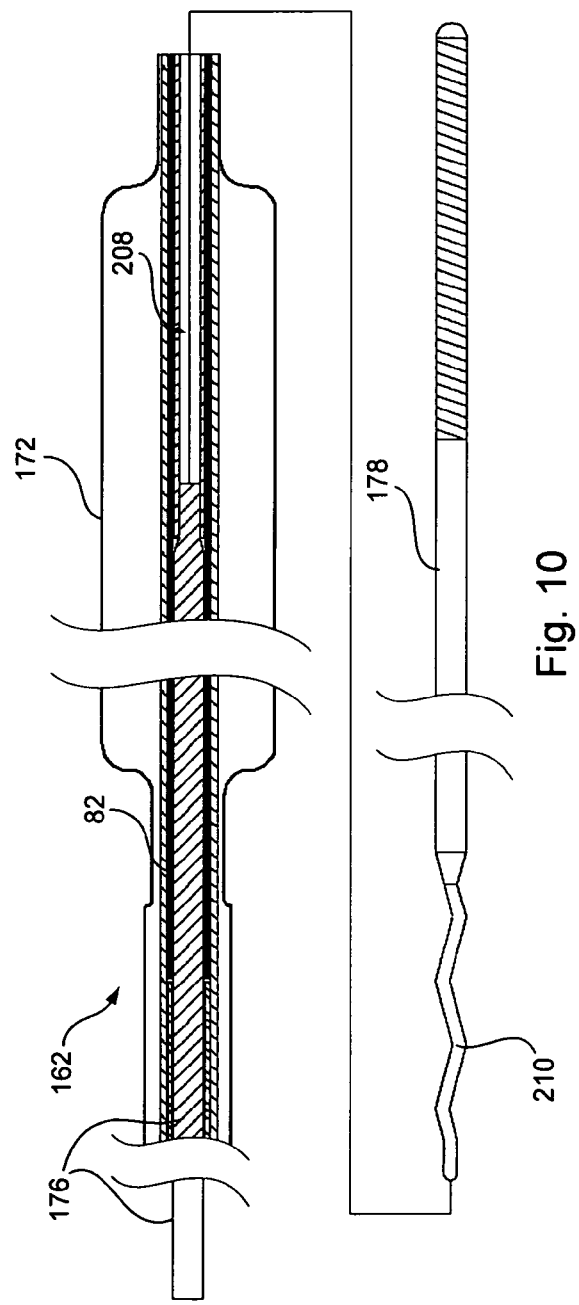

METHOD OF STENTING WITH MINIMAL DIAMETER GUIDED DELIVERY SYSTEMS

BACKGROUND

Implants such as stents and occlusive coils have been used in patients for a wide variety of reasons. One of the most common "stenting" procedures is carried out in connection with the treatment of atherosclerosis, a disease which results in a narrowing and stenosis of body lumens, such as the coronary arteries. At the site of the narrowing (i.e., the site of a lesion) a balloon is typically dilated in an angioplasty procedure to open the vessel. A stent is then set in apposition to the interior surface of the lumen in order to help maintain an open passageway. This result may be effected by means of the stent scaffolding support alone, or by virtue of the presence of one or more drugs carried by the stent to aide in the prevention of restenosis.

Various stent designs have been developed and used clinically, but self-expandable and balloon-expandable stent systems and their related deployment techniques are now predominant. Examples of self-expandable stents currently in use are the Magic WALLSTENT® stents and Radius stents (Boston Scientific). A commonly used balloon-expandable stent is the Cypher® stent (Cordis Corporation). Additional self-expanding stent background is presented in: "An Overview of Superelastic Stent Design," Min. Invas Ther & Allied Technol 2002: 9(3/4) 235-246, "A Survey of Stent Designs," Min. Invas Ther & Allied Technol 2002: 11(4) 137-147, and "Coronary Artery Stents: Design and Biologic Considerations," Cardiology Special Edition, 2003: 9(2) 9-14, "Clinical and Angiographic Efficacy of a Self-Expanding Stent" Am Heart J 2003: 145(5) 868-874.

A simple example of a self-expanding stent deployment system is described in U.S. Pat. No. 4,580,568 (Gianturco) in which a sheath restraining a stent overrides a pusher rod or tube. The reference shows a stent resiliently compressed in shape for delivery in which straight sections of the stent are arranged side-by-side and closely adjacent one another. Stents are delivered by passing them through the sheath using the pusher. No reference is made regarding use of a guidewire.

Other examples of self-expanding stent deployment systems are presented in U.S. Pat. No. 4,830,003 (Wolff, et al.) and U.S. Pat. No. 5,064,435 (Porter). In each, an outer sheath overriding an inner tubular member restrains a stent until the sheath is withdrawn. The tubular member has a lumen adapted to receive a guidewire and a distal end adapted to abut the stent for delivery. In these patents, the figures clearly illustrate the stent open to such an extent that it clearly will not interfere with passing the device over the guidewire used to navigated to the treatment site.

The ability to advance these systems over a guidewire is advantageous for a number of reasons. For one, the guidewire is the optimal device for navigating to and crossing a lesion. Also, the wire remains in place at the desired treatment site while the delivery system is simply advanced over the wire to reach the treatment site. Furthermore, medical practitioners become accustomed to using one or more particular guidewires.

Foregoing these advantages in hopes of achieving others, some inventors have sought to combine delivery device and guidewire functionality. One such system is described in U.S. Pat. No. 6,280,465 (Cryer). The device described in connection with FIG. 4 of Cryer includes a coil stent set upon a central guidewire member, over which a tubular sheath and pusher are disposed. In use, the combination is advanced to a treatment site within a guiding catheter as an integral assembly. U.S. Patent Application Publication No. 2003/0163156 (Hebert, et al.) describes a system that is indistinguishable from Cryer except in that the guidewire core carrying the stent integrally includes one or more stent interface features instead of using a separate pusher.

While these systems might be suitable for some applications, they cannot offer "true" guidewire performance. The multiple overlapping layers of a "guidewire" core, sheath, pusher (sometimes) and stent are too bulky to rival the performance of a true guidewire in terms of flexibility, torquability, navigation ability, etc.

Another class of sheath-based stent delivery systems seeks advantage through including an integral balloon. One such system is presented in the above-referenced Hebert application as well as U.S. Pat. No. 5,019,090 (Pinchuck) and U.S. Pat. No. 6,071,286 (Mawad). In each example, a distal balloon and a self-expanding stent is set upon a balloon catheter body, with a proximal sheath holding the stent until withdrawn. A reverse approach is shown in U.S. Pat. No. 5,192,297 (Hull) in which a sheath covers both a proximal balloon and a distal self-expanding stent.

Another type of combined self-expanding stent/balloon device is described in U.S. Pat. No. 6,702,843 (Brown, et al.) and U.S. Pat. No. 5,843,090 (Schuetz). In each, a stent is set upon an inner tubular member and held in a compressed configuration by an outer catheter body that includes a balloon. The stent is stabilized by a blocker associated with the inner tubular member so that upon withdrawal of the outer body (including the balloon), the stent is released.

PCT Publication No. US2004/008909 to Nikolchev et al. discloses yet another type of combined self-expanding stent/balloon device. Here, a stent is set over upon a core wire including a blocker element and received within the lumen of a balloon catheter to releasably restrain the stent.

Of all the balloon-combination devices described above, only the commonly-assigned PCT application described a system that delivers the stent directly upon a core wire. Each of the others sets the stent upon a tubular body for receiving a guidewire, thus severely limiting system miniaturization.

Still, the overall use of the '909 system is handicapped just as the Cryer and Hebert simple-sheath systems described above; none of these devices integrating a guidewire or guidewire-like body for the core can match the performance of an off-the-shelf guidewire for navigating tortuous anatomy. Accordingly, a need persists for stent space-efficient delivery systems with which a practitioner may still use a favored guidewire for navigation to a treatment site.

SUMMARY

The present invention includes over-the-wire (OTW) and Rapid-Exchange(RX) stent delivery systems comprising a catheter body having a near/proximal portion and a far/distal portion and a lumen extending therethrough. A self-expanding stent comprising near and far ends and a support structure extending therebetween is held in a compressed state within the delivery catheter lumen, typically being slidably compressed with the lumen.

The diameter of the catheter lumen and stent design is such that without some means of holding open one or more ends of the stent, that they will close-down—either fully or to such an extent that introducing a guidewire or pusher therein is impracticable. These means includes various wedge members. That is to say, structure is provided that interferes with other ones of the same (in the case of projections provided on the stent) or the stent itself. The later case is presented when the wedge member takes the form of a mandrel or introducer set at least partially within the stent. The mandrel may be a simple disposable length of rod or hypotubing or may be a portion of a standard or commercially-available guidewire or guidewire extension adapted to interface with a standard guidewire. The stent, which may be composed of a superelastic material, may directly contact the guidewire and be slidably thereover.

When not pre-assembled over such a wire or extension adapted to interface with a wire, various features may be provided to assist in introducing the delivery catheter over the wire (i.e., backloading the guidewire into the delivery system). In one variation, a removable introducer is provided; in another variation, the stent end is held open through interference between stent end wedge features.

In yet another variation, a mandrel with no other use holds the stent open. To aid in locating the guidewire proximal end within the stent, the mandrel is advantageously set back to create a pocket for receiving the end of the guidewire. Alternatively, the mandrel may extend from the delivery guide. In which case, it is advantageously includes a tapered end to interface with a complementary pocket in the guidewire.

Regardless of how the delivery catheter is set over the guidewire, once the catheter is advanced to the treatment site, the guidewire may be removed and a pusher introduced to stabilize the near side of the stent for delivery upon withdrawal of the catheter body.

Alternate approaches may be employed to stabilize the end of the stent as well. For example, the delivery system may include an elongate tubular member for abutting the stent. Still further, such a tube may be introduced over the guidewire and advanced within the catheter until it abuts the stent. Either way, the wire would not need to be removed in order to release the stent (e.g., by withdrawal of the catheter body while holding the stabilizing tube stationary).

Though not required, a highly advantageous option for the delivery system contemplates the inclusion of a balloon at or near the distal end of the device. Such a balloon may be adapted for use in an angioplasty/stenting procedure or be otherwise configured.

In another approach, the delivery system is sized for use within such a balloon catheter body as optionally employed in other variations of the invention. In which case, the delivery guide body typically comprises a simple sheath. To minimize sheath outer diameter and still allow for an OTW device, a smaller guidewire (e.g., 0.010 inch guidewire) may be used. Further, in view of the extremely small size of the system, the stent and delivery guide will often be mounted on the wire—typically an exchange length wire as elaborated upon below.

The subject methods may include each of the mechanical activities associated with implant release as well as dilatation activity. As such, methodology implicit to the use of the devices described forms part of the invention. Such methodology may include that associated with completing an angioplasty, bridging an aneurysm, deploying radially-expandable anchors for pacing leads or an embolic filter, or placement of a prosthesis within neurovasculature, an organ selected from the kidney and liver, within reproductive anatomy such as selected vasdeferens and fallopian tubes or other applications. In some methods, the various acts of implant release are considered; in others, delivery system loading and/or manufacture.

More particularly, a number of methods according to the present invention involve the manner in which the delivery system operates in reaching a treatment site. Other methods concern the manner in which the system is prepared for delivering an implant.

An example of the former class of methods includes stenting a body passageway by locating a guidewire at a site within the body passageway, introducing the delivery catheter onto the guidewire under circumstances in which the stent is held open to receive a guidewire, and feeding a delivery catheter over or along the guidewire.

An example of the latter class includes pre-assembly of the subject delivery catheter upon any of a standard guidewire with docking capability at a proximal end, an extension wire with docking capability at a distal end or an exchange-length wire. More generally, these methods include assembling the delivery system with such components as required to hold open the stent to easily allow feeding it (together with the delivery guide) over the guidewire.

Yet another class of methods includes the manner in which the delivery system is prepared to deliver a stent once it has reached the treatment site. Examples of these methods include the acts of exchanging the guidewire for a pusher and conversion of the guidewire to include a blocker. Also included is the act of feeding a balloon catheter over the delivery guide, in delivery systems designed for such use.

In a variation of the method(s), the above-described catheter body may comprise a balloon on its exterior, and the method further comprise dilating the body passageway by expanding the balloon at the site. It should be noted that dilatating the body passageway may occur either before and/or after stent delivery. Other methods are possible as well.

Also included in the invention are kits including the various constituent parts of the system and those that would inter-fit with it to provide the functionality described below. These may be provided in packaged combination, gathered by an end-user at a hospital site, etc.

The delivery systems described herein offer a number of advantages in their efficient construction and ability to deliver implants with or without coatings in highly challenging applications. Those with skill in the art may appreciate further benefits or advantages of the subject inventive variations.

DEFINITIONS

The term "stent" as used herein includes any stent, such as coronary artery stents, other vascular prosthesis, or other radially expanding or expandable prosthesis, or scaffold-type implant suitable for the noted treatments or otherwise. Exemplary structures include wire mesh, ring or lattice. A "self-expanding" stent as used herein is a scaffold-type structure (serving any of a number of purposes) that expands from a reduced-diameter (be it circular or otherwise) configuration to an increased-diameter configuration. The mechanism for shape recovery may be elastic or pseudoelastic. While it is generally desirable to employ an alloy (such as nickel-titanium, or Nitinol alloy) set for use as a superelastic alloy, the material may alternatively employ thermal shape memory properties to drive expansion upon release.

A "wire" as used herein generally comprises a common metallic member such as made of stainless steel or another material. The wire may be at least partially coated or covered by a polymeric material (e.g., with an insulating polymer such as Polyamide, or a lubricious material such as TEFLON®, i.e., PolyTetraFluoroEthylene or PTFE). Still further, the "wire" may be a hybrid structure with metal and a polymeric material (e.g., Vectran™, Spectra™, Nylon, etc.) or composite material (e.g., carbon fiber in a polymer matrix). The wire may be in the form of a filament, bundle of filaments, coaxial core with cladding, cable, ribbon or in some other form. It is generally not hollow. The wire may comprise different segments of material along an overall length.

A "guidewire" may comprise any guidewire commonly used to access sites within the vasculature or in another medical procedure. An "exchange length" guidewire is typically double the length of a common wire. Such length allows a practitioner to maintain a hold upon the guidewire regardless of the position of a catheter body received over the guidewire. A guidewire "extension" or "extension wire" is an elongate wire member suited for "docking" with the guidewire to provided an "extension length" assembly. The guidewire may include features to couple the guidewire to an extension or facilitate entry into a far end a delivery. Examples of such extensible hardware are presented in U.S. Pat. No. 4,827,941 (Taylor et al.)

A "pusher" or "blocker" is a device that prevents the stent from moving with a delivery catheter as the catheter body or another sheath is withdrawn from the stent. The pusher acts to stabilize the proximal end of the stent. The pusher may have a shoulder or another abutment feature or features as well as a conical tip or reduced diameter tip stepped-down from the outer diameter. The "pusher" may indeed be used to push the stent from the delivery catheter. More often, irrespective of what the name may imply, it is simply held stationary with respect to the vessel and used to stabilize the position of the stent as the sheath/catheter body moves relative to it and the stent.

A "mandrel" is an elongate member that fits within a portion or all of the stent to maintain an open configuration. The mandrel may be tubular or solid. It may comprise a portion of a guidewire or extension wire, thereby optionally offering dual use. The mandrel may alternatively comprise a disposable element pushed out of the delivery catheter thereby only serving as a place holder.

A "hypotube" or "hypotubing" as referred to herein means small diameter tubing in the size range discussed below, generally with a thin wall. The hypotube may specifically be hypodermic needle tubing. Alternatively, it maybe wound or braided cable tubing, such as provided by Asahi Intec Co., Ltd. or otherwise. As with the "wire" discussed above, the material defining the hypotube may be metallic, polymeric or a hybrid of metallic and polymeric or composite material.

BRIEF DESCRIPTIONS OF THE DRAWINGS

The figures provided herein are not necessarily drawn to scale, with some components and features being exaggerated for clarity. Each of the figures diagrammatically illustrates aspects of the invention. Of these:

FIGS. 3A-3E show a portion of a stent as described in FIGS. 2A-2D, illustrating aspects of stent compression;

FIGS. 6A and 6B are partial cross-sectional illustrations of variations of working ends of delivery systems with mandrels placed within stents according to the present invention;

FIG. 8A is a partial cross-sectional view with a distal end of the stent wedged open by end features on the stent; FIG. 8B shows the end of the stent taken along line 8B-8B in FIG. 8A; and FIG. 8C shows a plan view of a wedge feature for either end of a stent for maintaining an opening when the stent is in a compressed state;

FIG. 9 is a partial cross-sectional view of a variation of the invention where the mandrel portions holding open the stent comprises part of a guidewire;

FIG. 10 is a partial cross-sectional view of a variation of the invention where the mandrel portions holding open the stent comprises a guidewire extension;

Variation of the invention from the embodiments pictured is contemplated.

DETAILED DESCRIPTION OF THE INVENTION

Various exemplary embodiments of the invention are described below. Reference is made to these examples in a non-limiting sense. They are provided to illustrate more broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

Self-Expanding Stent Designs and Opportunities

Figure 1:
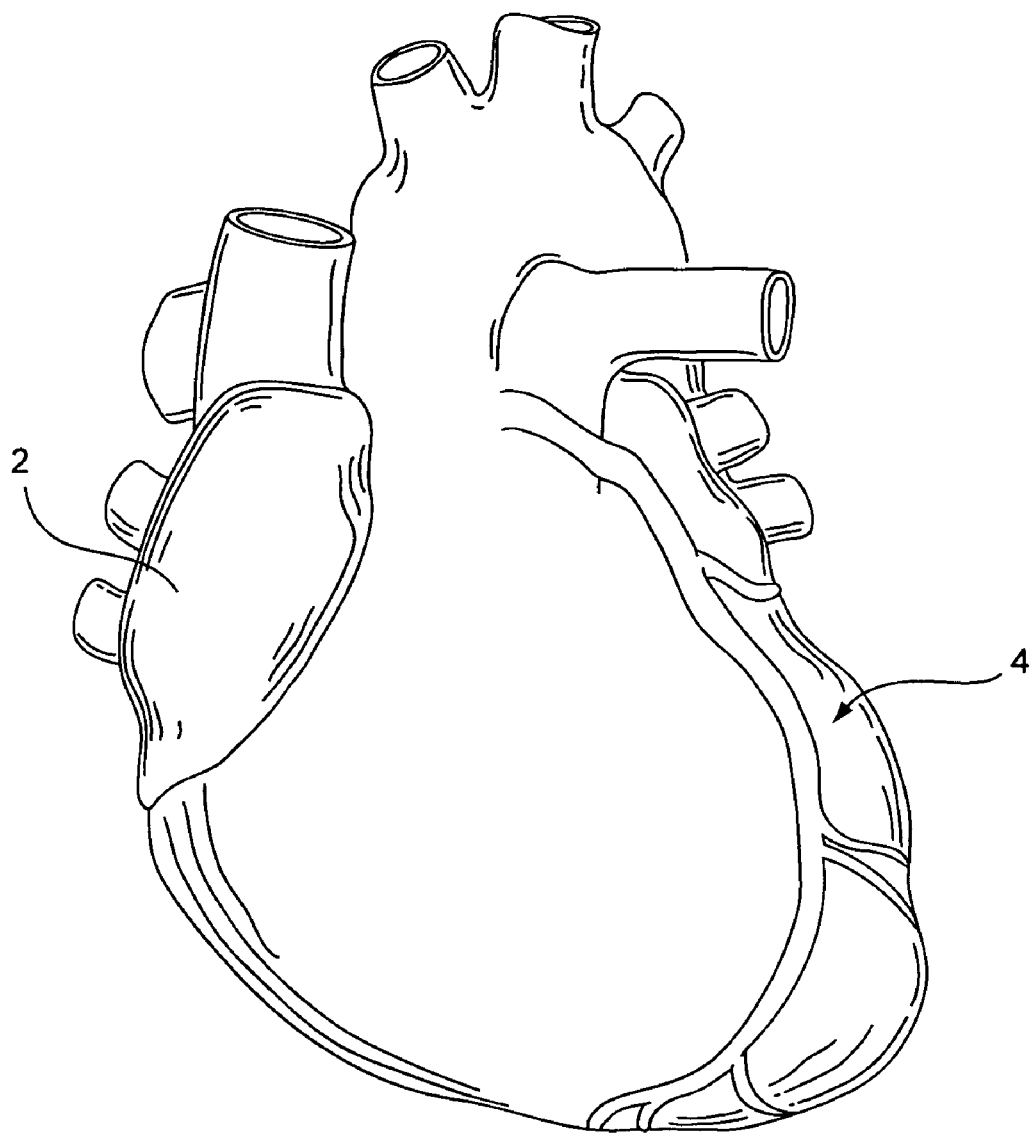
FIG. 1 shows a heart in which its vessels may be the subject of one or more angioplasty and stenting procedures.

In light of this framework, FIG. 1 shows a heart 2 in which its vessels may be the subject of one or more angioplasty and/or stenting procedures. To date, however, significant difficulty or impossibility is confronted in reaching smaller coronary arteries 4. If a stent and a delivery system could be provided for accessing such small vessels and other difficult anatomy, an additional 20 to 25% of percutaneous coronary procedures could be performed with such a system. Such potential offers opportunity for huge gains in human healthcare and a concomitant market opportunity—with the further benefit of avoiding loss of income and productivity of those treated.

Features of the present invention are uniquely suited for a system able to reach small vessels (though use of the subject systems is not limited to such a setting.) By "small" vessels, it is meant vessels having an inside diameter from between about 1.5 to 2 mm and up to about 3 mm in diameter. These vessels include, but are not limited to, the Posterior Descending Artery (PDA), Obtuse Marginals (OMs) and small diagonals. Conditions such as diffuse stenosis and diabetes produce situations that represent other access and delivery challenges that can be addressed with a delivery system according to the present invention. Other extended treatment areas addressable with the subject systems include vessel bifurcations, chronic total occlusions (CTOs), and prevention procedures (such as in stenting of vulnerable plaque).

It may be preferred to use a drug eluting stent (DES) in such an applications to aid in preventing restenosis. A review of suitable drug coatings and available vendors is presented in "DES Overview: Agents, release mechanism, and stent platform" a presentation by Campbell Rogers, MD incorporated by reference in its entirety. However, bare-metal stents may be employed in the present invention.

Examples of various therapeutic agents that may be used in or on the subject prosthesis include, but are not limited to, antibiotics, anticoagulants, antifungal agents, anti-inflammatory agents, antineoplastic agents, antithrombotic agents, endothelialization promoting agents, free radical scavengers, immunosuppressive agents, antiproliferative agents, thrombolytic agents, and any combination thereof. The therapeutic agent may be coated onto the implant, mixed with a biodegradable polymer or other suitable temporary carrier and then coated onto the implant, or (when the implant is made from a polymeric material) dispersed throughout the polymer. The agent can be directly applied to the stent surface(s) as a continuous coating or in discrete droplets, introduced into pockets or an appropriate matrix set over at least an outer portion of the stent, etc.

While some might argue that the particular role and optimal usage of self expanding stents has yet to be defined, they offer an inherent advantage over balloon expandable stents. The latter type of devices produce "skid mark" trauma (at least when delivered uncovered upon a balloon) and are associated with a higher risk of end dissection or barotraumas caused at least in part by high balloon pressures and related forces when deforming a balloon-expandable stent for deployment to account for recoil upon balloon deflation.

Yet, with an appropriate deployment system, self-expanding stents may offer one or more of the following advantages over balloon-expandable models: 1) greater accessibility to distal, tortuous and small vessel anatomy—by virtue of decreasing crossing diameter and increasing compliance relative to a system requiring a deployment balloon, 2) sequentially controlled or "gentle" device deployment, 3) use with low pressure balloon pre-dilatation (if desirable) to reduce barotraumas, 4) strut thickness reduction in some cases reducing the amount of "foreign body" material in a vessel or other body conduit, 5) opportunity to treat neurovasculature—due to smaller crossing diameters and/or gentle delivery options, 6) the ability to easily scale-up a successful small vessel treatment system to treat larger vessels or vice versa, 7) a decrease in system complexity, offering potential advantages both in terms of reliability and system cost, 8) reducing intimal hyperplasia, and 9) conformability to tapering anatomy—without imparting complimentary geometry to the stent (though this option exists as well).

Figure 2A:
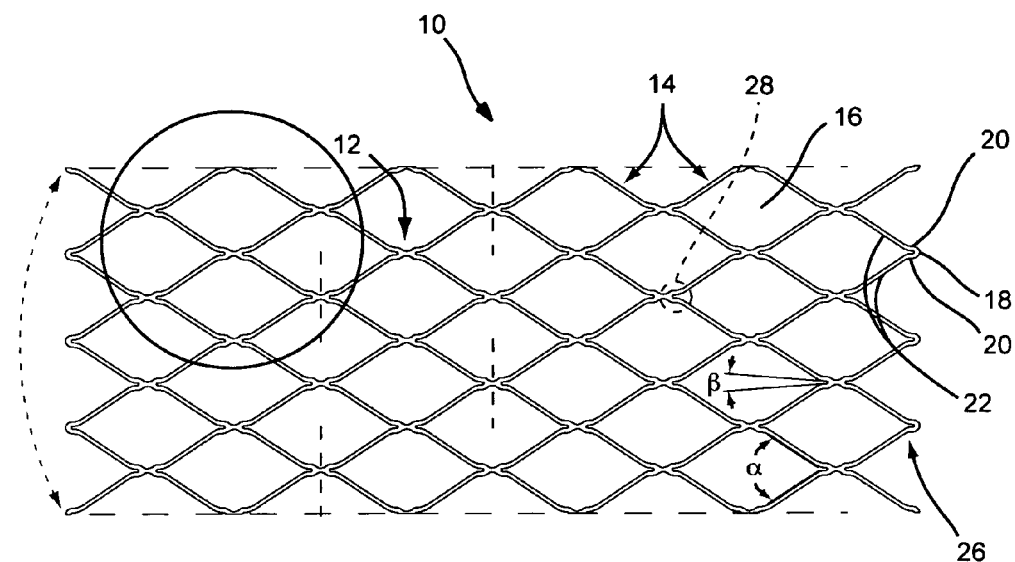
FIGS. 2A and 2B show a first expanded stent cut pattern and an expanded view of a section of the same, respectively.

At least some of these noted advantages may be realized using a stent 10 as shown in FIG. 2A. The stent pattern pictured is well suited for use in small vessels. It may be collapsed to an outer diameter of about 0.018 inch (0.46 mm), 0.014 inch (0.36 mm) or even smaller—and expanded to a size (fully unrestrained) between about 1.5 mm (0.059 inch) or 2 mm (0.079 inch) or 3 mm (0.12 inch) and about 3.5 mm (0.14 inch).

In use, the stent will be sized so that it is not fully expanded when fully deployed against the wall of a vessel in order to provide a measure of radial force thereto (i.e., the stent will be "oversized" relative to the vessel diameter). The force will secure the stent and offer potential benefits in reducing intimal hyperplasia and vessel collapse, or even pin dissected tissue in apposition.

Stent 10 preferably comprises NiTi that is superelastic at or below room temperature (i.e., as in having an Af as low as 15 degrees C. or even 0 to −15 degrees C.). Also, the stent is preferably electropolished to improve biocompatibility and corrosion and fatigue resistance. The stent may be a DES unit as referenced above. The stent may be coated with gold and/or platinum or any other biocompatible radiopaque substance to provide improved radiopacity for viewing under medical imaging. It may be biodegradable.

In a stent adapted for compression to an outer diameter of about 0.014 or about 0.018 inches and expand to about 3.5 mm, the thickness of the NiTi is about 0.002 to about 0.003 inches (0.5-0.8 mm). Such a stent is designed for use in about a 3 mm vessel or other body conduit, thereby providing the desired radial force in the manner noted above. Further information regarding radial force parameters in coronary stents may be noted in the article, "Radial Force of Coronary Stents: A Comparative Analysis," Catheterization and Cardiovascular Interventions 46: 380-391 (1999), incorporated by reference herein in its entirety.

In one manner of production, the stent in FIG. 2A is laser or EDM cut from round NiTi tubing, with the flattened-out pattern shown wrapping around the tube as indicated by dashed lines. In such a procedure, the stent is preferably cut in its fully-expanded shape. By initially producing the stent to full size, the approach allows cutting finer details in comparison to simply cutting a smaller tube with slits and then heat-setting/annealing it into its final (working) diameter. Still, stents used in the present invention may be cut in under-sized tubing and then heat-set into a larger diameter as need be.

Figure 2B:
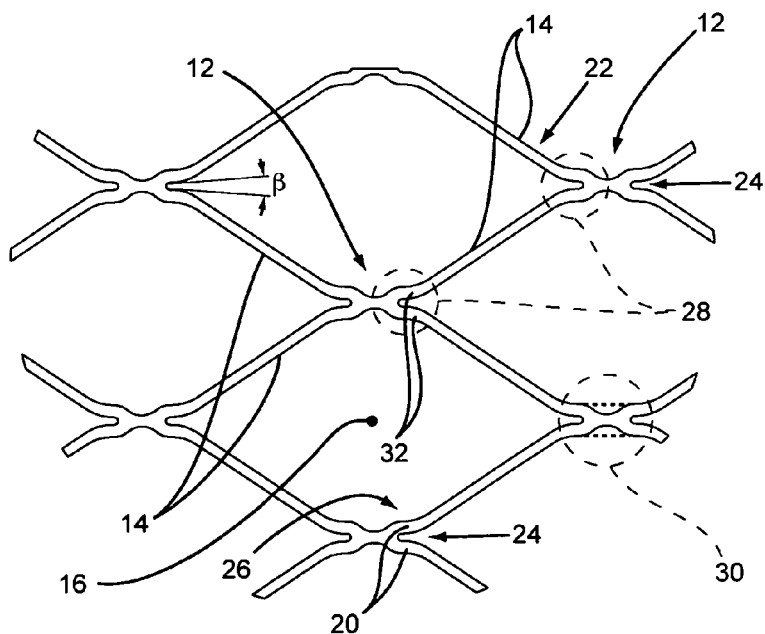

Regarding the finer details of the subject stent, as readily observed in the detail view provided in FIG. 2B, necked down bridge sections 12 are provided between axially/horizontally adjacent struts or arms/legs 14, wherein the struts define a lattice of closed cells 16. In certain variations of the invention, however, the bridge sections can be strategically separated or opened as indicated by the broken lines in FIG. 2A. Doing so disrupts the closed cell pattern discussed above, but may increase stent conformability to tortuous anatomy. In any case, to facilitate such tuning of the stent, the bridge sections are preferably sufficiently-long so that fully rounded ends may be formed internally to the lattice just as shown at terminal ends or crowns 18 of the cells (i.e., like those ends not carrying wedge-type interface features as described below to maintain one or more of the stent ends in an open configuration.)

As for the optional double-concave profile of each strut bridge 12 shown, this form is advantageous in that it reduces material width (relative to what would otherwise be presented by a parallel side profile) to improve flexibility and thus trackability and conformability of the stent within the subject anatomy while still maintaining the option for separating/breaking the cells apart. Whether cut to provide rounded end portions or adjoined by a bridge section 12, strut junction sections 28 connect circumferentially or vertically adjacent struts (as illustrated). Where no bridge sections are provided, the junction sections can be unified between horizontally adjacent stent struts as indicated in region 30.

Further optional features of stent 10 are employed in the strut junction sections 28 of the design. Specifically, strut ends 20 increase in width relative to medial strut portions 22. Such a configuration distributes bending (during collapse of the stent) preferentially toward the middle region of the struts. For a given stent diameter and deflection, longer struts allow for lower stresses within the stent (and, hence, a possibility of higher compression ratios). Shorter struts allow for greater radial force (and concomitant resistance to a radially applied load) upon deployment.

In order to increase stent compliance for higher compression ratios. accommodation is made for the stiffer strut ends 20 provided in the design shown in FIG. 2A. Namely, the gap 24 between the strut ends 22 is set at a smaller angle as if the stent were already partially collapsed in that area. Thus, the smaller amount of angular deflection that occurs at ends 20 can bring the sections parallel (or nearly so) when the strut medial portions 22 are so-arranged. In the variation of the invention in FIG. 2A, radiused or curved sections 26 provide a transition from a medial strut angle α (ranging from about 85 degrees to about 60 degrees) to an end strut angle β (ranging from about 30 to about 0 degrees) at the strut junctions 28 and/or extensions therefrom.

In addition, it is noted that gap 24 an angle β may actually be configured to completely close prior to fully collapsing angle α. The value of doing so would be to limit the strains (and hence, stresses) at the strut ends 22 and cell end regions 18 by providing a physical stop to prevent further strain.

In the detail view of FIG. 2B, angle β is set at 0 degrees. The gap 24 defined thereby by virtue of the noticeably thicker end sections 20 at the junction result in very little flexure along those lever arms. The strut medial portions are especially intended to accommodate bending. In addition, a hinging effect at the corner or turn 32 of junction section 28 may allow the strut to swing around angle α to provide the primary mode for compression of the stent.

Figure 2C:
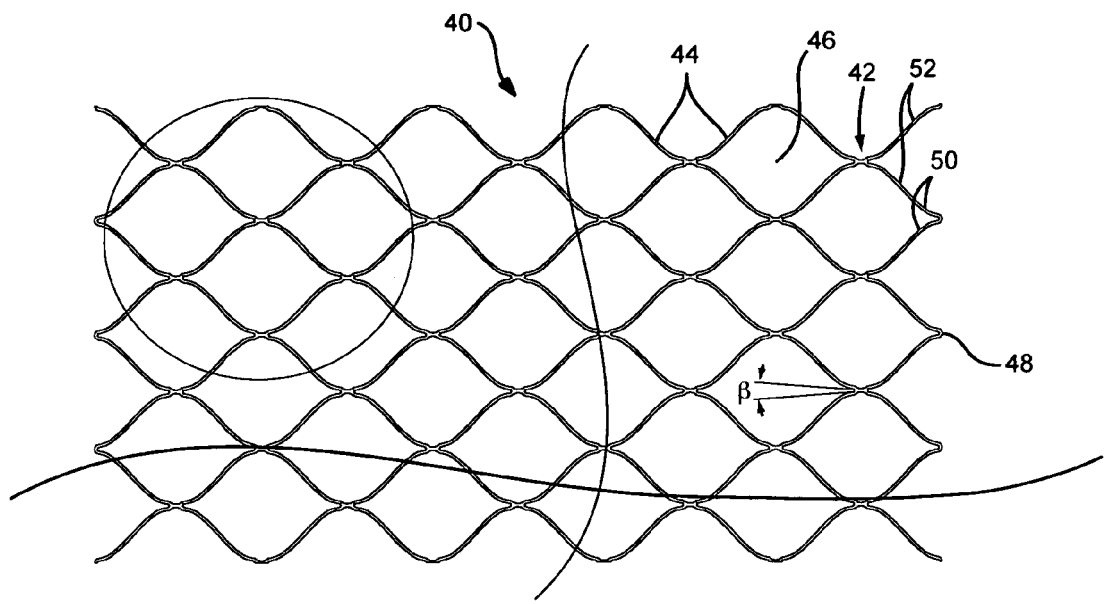
FIGS. 2C and 2D show a second expanded stent cut pattern and an expanded view of a section of the same, respectively.
Figure 2D:
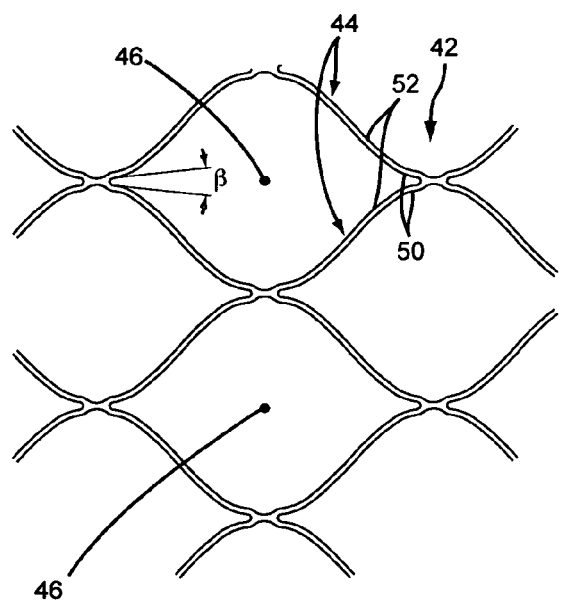

The stent pattern 40 shown in FIG. 2C and detailed in FIG. 2D offers certain similarities as well as some major differences from the stent pattern presented in FIGS. 2A and 2B. As in the variation above, the pattern includes necked down bridge sections 42 between adjacent struts or arms/legs 44, wherein the struts define a lattice of closed cells 46. In addition, terminal ends or crowns 48 of the cells are preferably rounded-off so as to be atraumatic.

Furthermore, the bridge sections 42 of stent 82 can be separated for compliance purposes. In addition, they may be otherwise modified (e.g., as described above) or even eliminated. Also, in each design, the overall dimensions of the cells and indeed the number of cells provided to define axial length and/or diameter may be varied (as indicated by the vertical and horizontal section lines in FIG. 2C).

Like the previous stent design, strut ends 50 may offer some increase in width relative to medial strut portions 52. However, as shown in FIG. 2D, as compared to FIG. 2B, the angle β is typically larger. Such a configuration is not concerned with developing a hinge section and a relatively stiffer outer strut section. Instead, angle β in the FIG. 2C/2D design is meant to collapse and the strut ends are meant to bend in concert with the medial strut portions so as to essentially straighten-out upon collapsing the stent, generally forming tear-drop spaces between adjacent struts. This approach offers a stress-reducing radius of curvature where struts join, and maximum stent compression.

The "S" curves defined by the struts are produced in a stent cut to a final or near final size (as shown in FIGS. 2C and 2D). The curves are preferably determined by virtue of their origination in a physical or computer model that is expanded from a desired compressed shape to the final expanded shape. So derived, the stent can be compressed or collapsed under force to provide an outer surface profile that is as solid or smooth and/or cylindrical as possible or feasible when set upon a mandrel. Such action is enabled by distribution of the stresses associated with compression to generate strains to produce the intended compressed and expanded shapes. This effect is accomplished in a design unaffected by one or more expansion and heat setting cycles that otherwise deteriorate the quality of the superelastic NiTi stent material. Further details regarding the "S" stent design and alternative stent constructions as may be used in the present invention are disclosed in U.S. patent application Ser. No. 11/238,646 entitled, "Small Vessel Stent Designs", filed Sep. 28, 2005 and incorporated herein by reference in its entirety.

Since each of the above stent designs account for problematic strain (and in the latter case actually uses the same to provide an improved compressed profile), very high compression ratios of the stent may be achieved from about 5× to about 10× or above. Still, in achieving such compression ratios, certain features of the stent have been observed leading to what would present problems in OTW use if not solved by the various approaches taught by the current invention.

Specifically, when a stent cut according to the patterns above are compressed without being set upon a mandrel a seemingly unusual characteristic is displayed. Namely, the stents do not compress evenly in apposition with the tube that is constraining them. Neither are the highest stress areas (the junction between struts) in contact with the tube, where it might seem they should be located in order to achieve a more uniform stress distribution.

Rather, the highest stress area drive or dip inwards away from the constraining outer diameter. In other words the near and far ends of the stent (crowns 18) and bridges 12 between adjacent cells 16 dive toward the open center of the stent. Such action (at least at the ends) interferes with the ability to use a stent so-compressed in an OTW system because the collapsed far end of the stent can be too difficult to practicably (i.e., acceptably within an operating room) receive a guidewire.

While seemingly mysterious at first, this action of the stent that the current invention addresses in OTW and RX systems can be explained by a geometric/trigonometric analysis of strut behavior. FIGS. 3A-3E offer the appropriate context.

These figures provide different views of a single strut of a stent as may be used in the current invention as it is translated from an initial state "I" at an outer diameter "OD" of a relaxed stent to a compressed state "C" at an inner, compressed diameter "ID" as within a delivery device. In the initial state (I), the strut is set at an angle across the cylindrical body of the stent. When the stent is compressed, the orientation of the strut changes. It is angled more closely to the axis of the stent body. As such, a lengthening effect is observed along the entire length of the stent. When releasing a stent, loss of this effect is referred to as "foreshortening". In any case, this lengthening "L" is evident in FIGS. 3C and 3D as illustrated by the ID circle that is dropped down.

The effect of greatest interest, however, is best illustrated in FIG. 3E. In this plan view drawing, as the strut is turned and moved inward it retains its curvature. This curvature equates to a width "W" dictating the degree to which the strut bows outward along its length from its endpoints at the ID. With repeated strut units circumscribing the ID, an outer envelope "OE" of the compressed stent is defined by the arcuate struts.

Certainly, their shape will be modified when subject to an external load (e.g., a tubular restraint). However, the general dipping or hour-glass shape resultant of the initial strut geometry remains in physical samples tested and as further demonstrated by Finite Element Analysis (FEA) models generated for the assignee hereof when the stent is not fully sandwiched between an outer restraint and inner mandrel. In a number of ways, the present invention accounts for this fact.

Angioplasty and Stenting Procedure

As for the manner of using the inventive system as optionally configured,

FIGS. 4A-4H illustrate an exemplary angioplasty procedure. Still, the delivery systems and stents or implants described herein may be used otherwise—especially as specifically referenced herein.

Figure 4A:
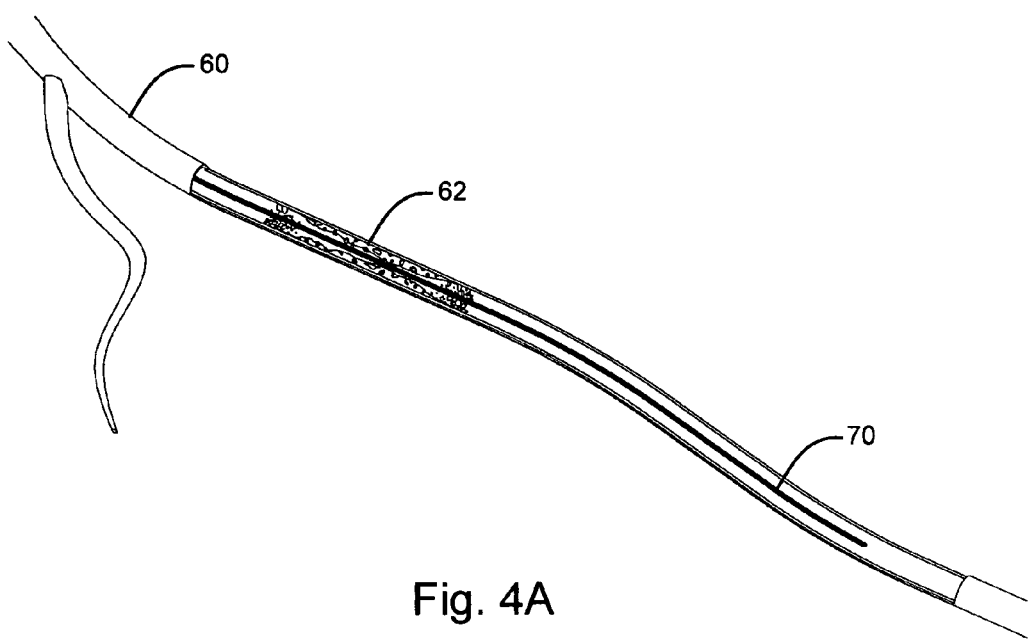
FIGS. 4A-4H show stent deployment hardware and methodology for carrying out an angioplasty and stenting procedure.
Figure 4B:
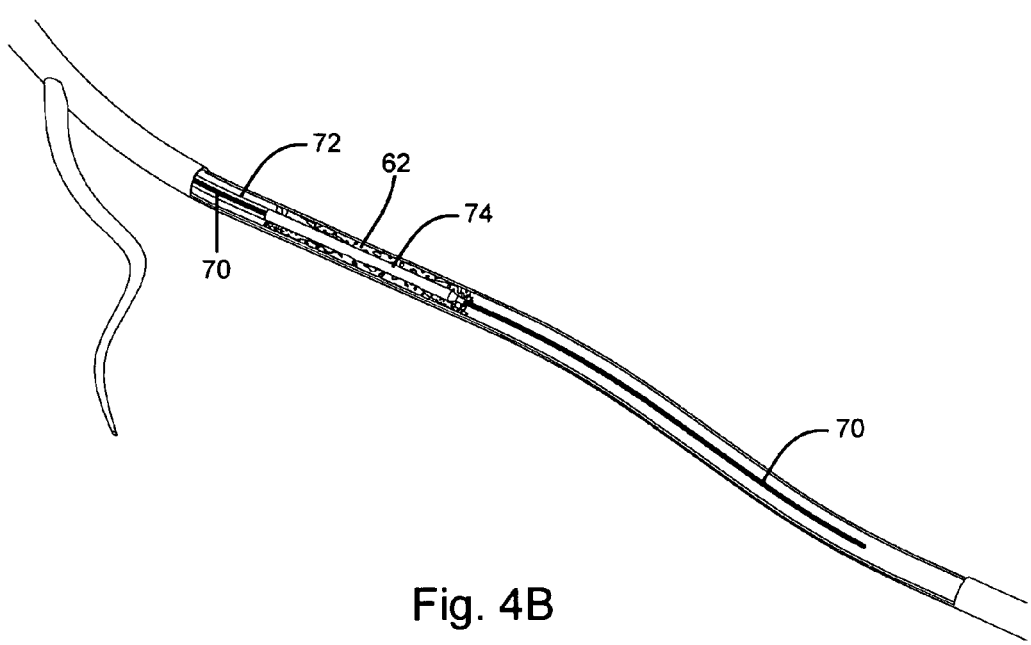

Turning to FIG. 4A, it shows a coronary artery 60 that is partially or totally occluded by plaque at a treatment site/lesion 62. Into this vessel and typically using fluoroscopy, a guidewire 70 is passed distal to the treatment site. In FIG. 4B, an over-the-wire ("OTW") delivery/balloon catheter 72 with a balloon tip 74 is passed over the guidewire, aligning the balloon portion with the lesion (the balloon catheter shaft proximal to the balloon is shown in cross section with guidewire 70 therein).

Figure 4C:
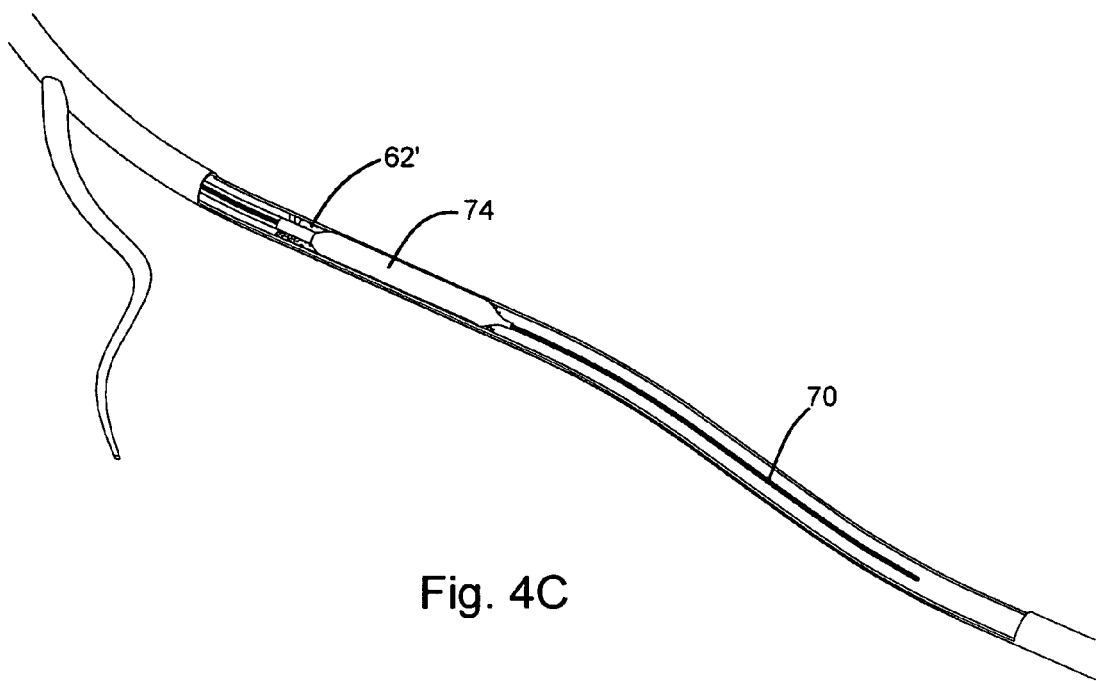
Figure 4D:
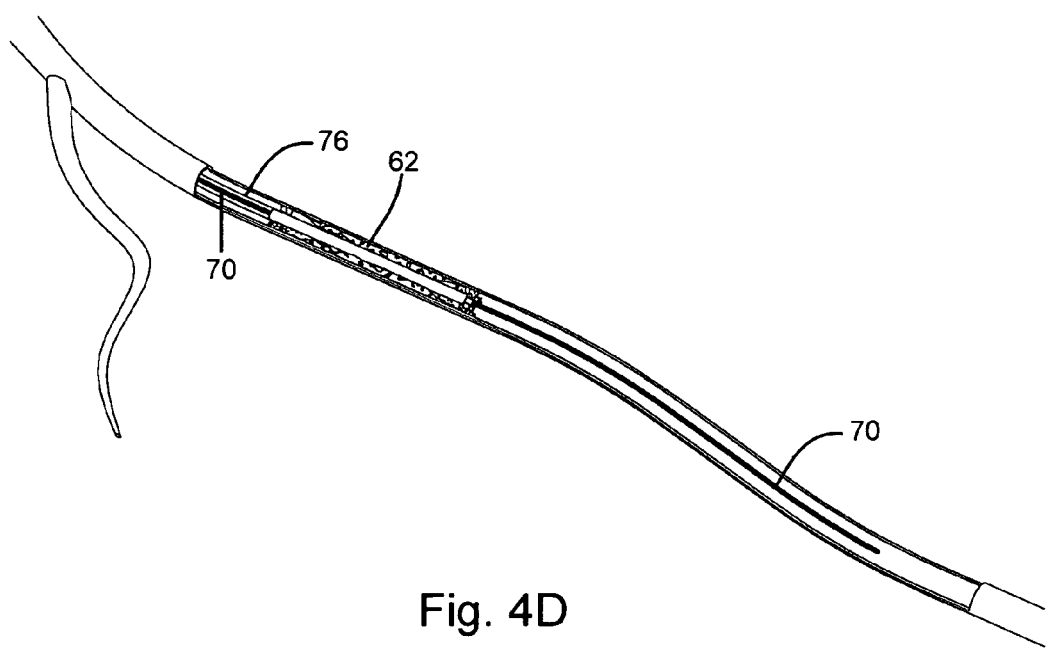
Figure 4E:
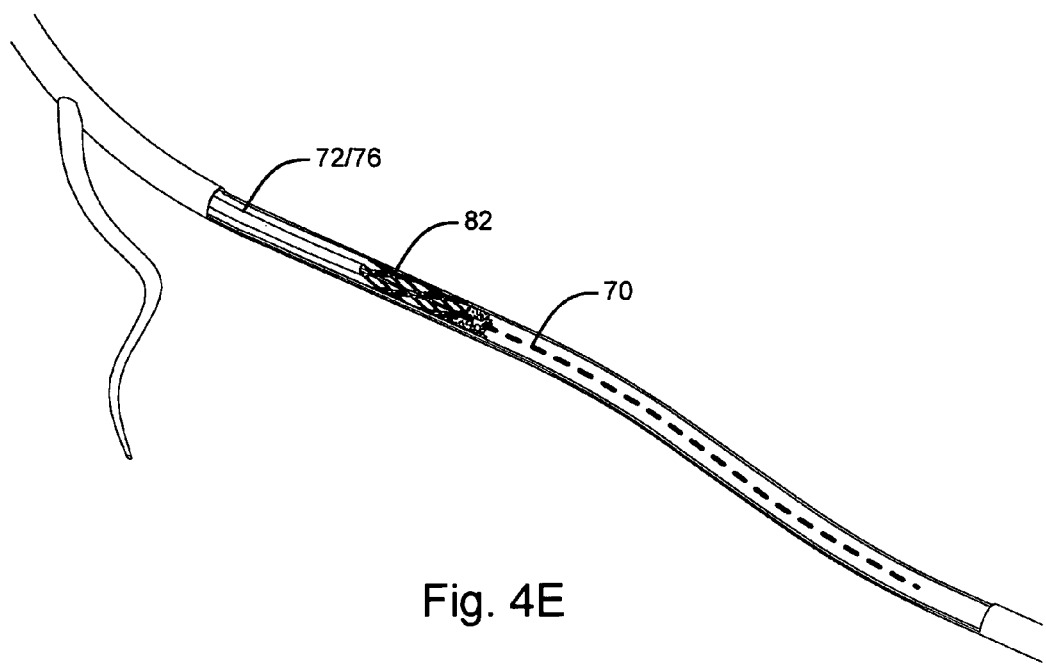

As illustrated in FIG. 4C, balloon 74 is expanded (dilatated or dilated) in performing an angioplasty procedure, opening the vessel in the region of lesion 62. The balloon expansion may be regarded as "predilatation" in the sense that it will be followed by stent placement (and optionally) a "postdilatation" balloon expansion procedure.

Next, the balloon is at least partially deflated. When the balloon catheter is not an integral part of the stent delivery system, it is exchanged for one. To do so, the delivery catheter 76 is introduced over-the-wire and advanced to the site of the lesion 62 in a manner appropriate to the variation of the invention offered as described below. Such a scenario is pictured in FIG. 4D. Then one or more stents are delivered by withdrawing the balloon/delivery catheter body/sheath 72/76 as shown in FIG. E. In connection with this, guidewire 70 may remain in place or be withdrawn. This option is indicated by showing the guidewire in broken line.

Figure 4F:
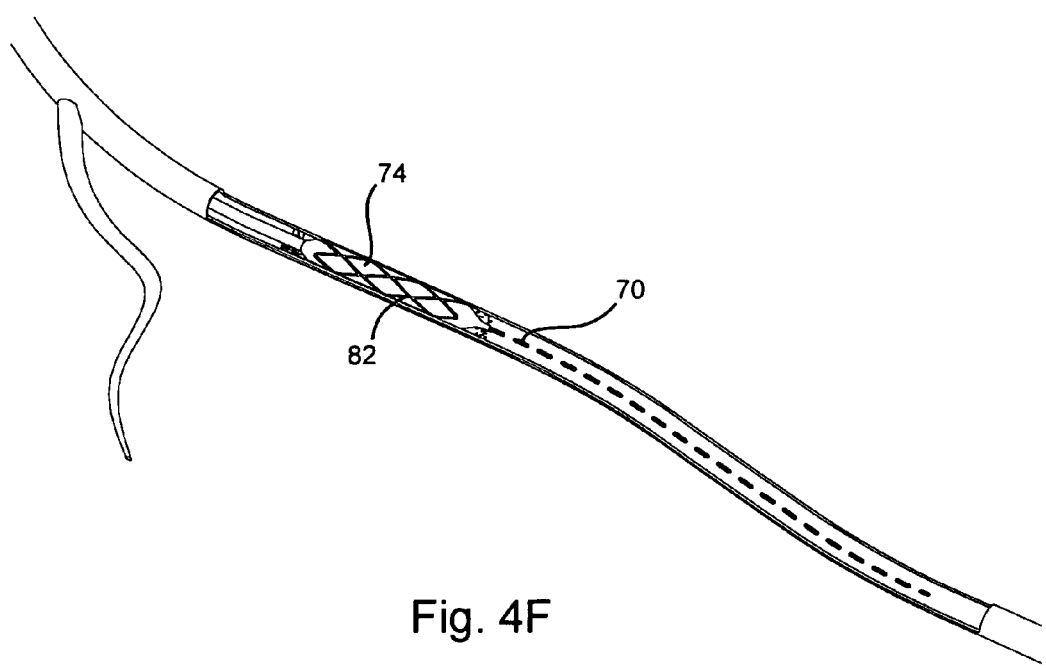

Another scenario according to the present invention is offered when the balloon catheter body serves dual use to offer a sheath for restraining the stent in a delivery system. In which case, withdrawal of the balloon catheter body effects stent release. Post-dilatation may then be accomplished by re-advancing at least the balloon portion of the device (when an integral-balloon device is used) where the stent has been delivered and then inflating the balloon. Such action is shown in FIG. 4F. The same figure may also be viewed as depicting an act within a method of treatment in which a balloon catheter has been introduced after withdrawal for a delivery system including no integral balloon.

Regardless of which approach is employed, during stent delivery, a pusher rod or full or partial length tube within the delivery guide stabilizes the proximal end 84 of the stent while the sheath (with or without a balloon thereon) is withdrawn to progressively release the self-expanding scaffold. Upon deployment, stent 82 assumes an at least partially expanded shape in apposition to the compressed plaque 62'. When postdilatation is employed by, again, introducing a balloon and inflating it within the stent as shown in FIG. 4F, this procedure may further expand the stent, pushing it into adjacent plaque—helping to secure each. However, the balloon section need not be reintroduced or repositioned for postdilatation.

Figure 4G:
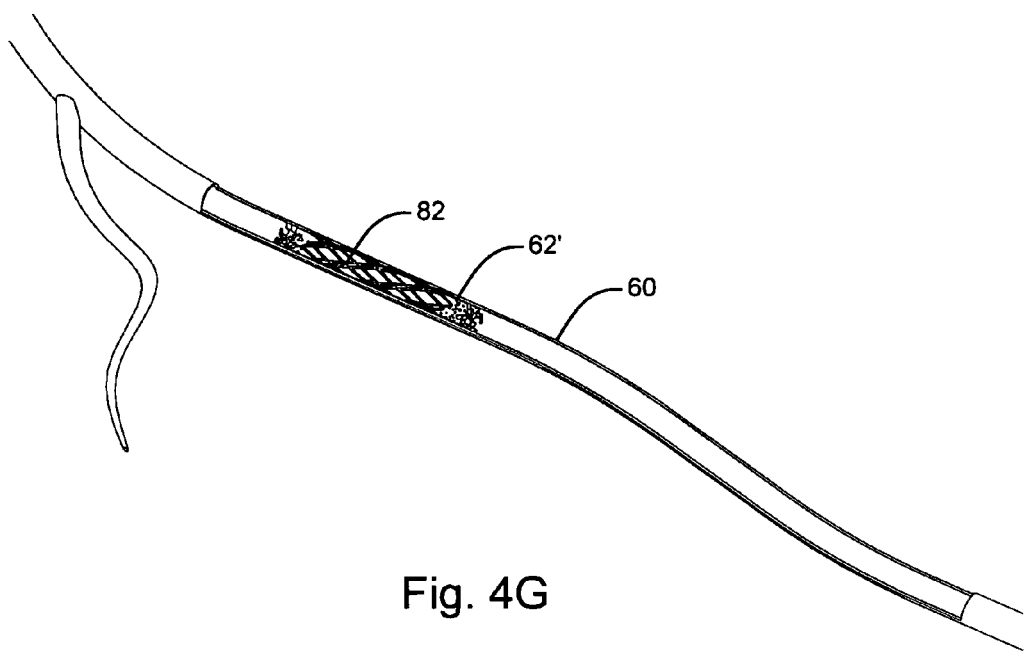
Figure 4H:
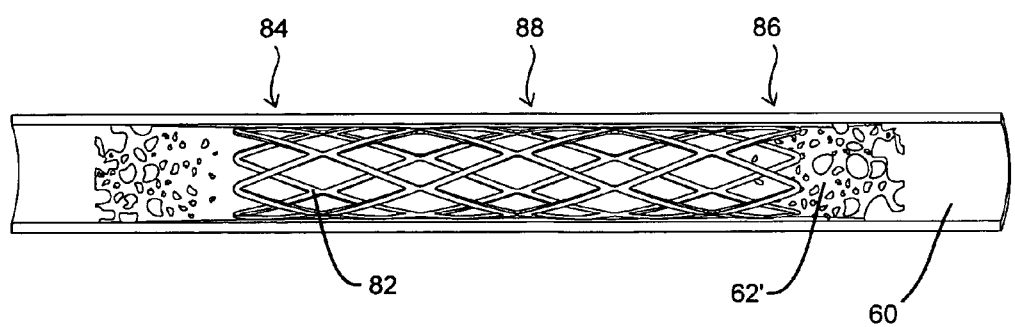

Once the balloon catheter or delivery device and guidewire 70 are withdrawn as shown in FIG. 4G, the angioplasty and stenting procedure at the lesion in vessel 60 is complete. FIG. 4H shows a detailed view of the emplaced stent and the desired resultant product in the form of a supported, open vessel. All of the near or proximal end 84, far or distal end 86 and a main body or support structure 88 of the stent extending therebetween is in apposition with tissue or plaque at the site of the lesion.

In any case, it is to be recognized that the subject invention may be practiced to perform "direct stenting." That is, a stent may be delivered alone to maintain a body conduit, without preceding balloon angioplasty. Likewise, once one or more stents are delivered with the subject system (either by a single system, or by using multiple systems) the post-dilatation procedure(s) discussed above are merely optional. In addition, other endpoints may be desired such as implanting an anchoring stent in a hollow tubular body organ, closing off an aneurysm, delivering a plurality of stents, etc. In performing any of a variety of these or other procedures, suitable modification will be made in the subject methodology. The procedure shown is depicted merely because it illustrates a preferred mode of practicing the subject invention, despite its potential for broader applicability.

Delivery System Overview

Figure 5:
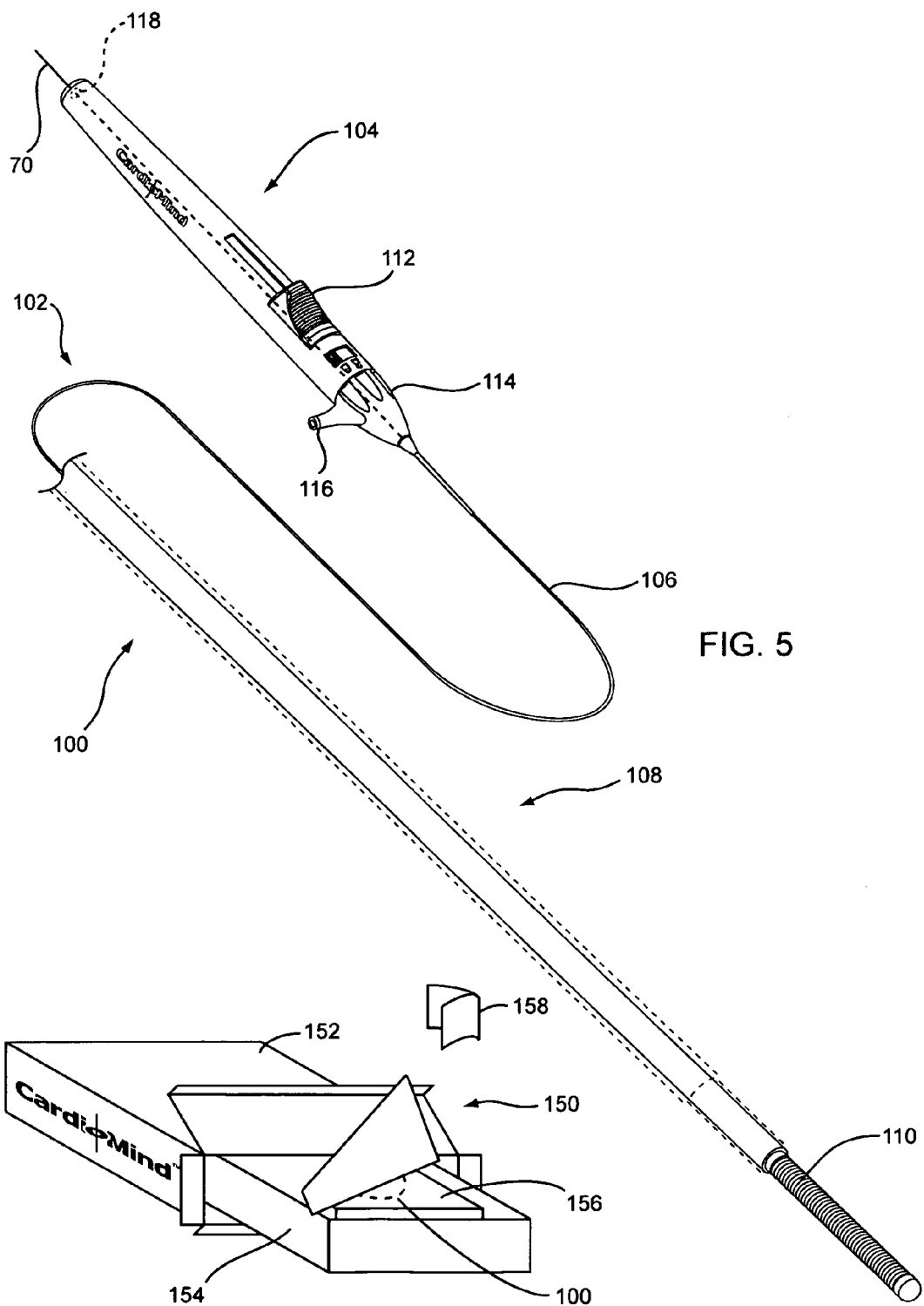
FIG. 5 shows an overview of a delivery system according to the present invention.

An overview of an implant delivery system according to the invention is presented in FIG. 5. Here an implant delivery system 100 is shown as including an OTW delivery catheter 102 with a handle 104, a catheter body 106 with a distal implant carrying section 108. A guidewire terminating in an atraumatic coil tip 110 is shown within the delivery catheter.

The handle may include one or more of a lockable lever, trigger, knob, wheel, slider 112 etc. actuating withdrawal of the catheter body relative to the stent. Furthermore, a removable interface member 114 may be provided to facilitate taking the handle off of the delivery system.

Still further, the catheter body may be that of a balloon catheter incorporating a balloon portion 116 (indicated as optional by broken line) and fluid lumen in communication therewith. To facilitate use of the system over an exchange-length wire, the handle may include a proximal pass-through 118. In such a case, a fluid delivery port 116 may be incorporated in the handle 104 or other portion of the device accessible to the medical practitioner.

A number of delivery system examples are provided below. Sections of systems are shown that can be mixed-and-matched with others (both in configurations shown and others as may be apparent to one with skill in the art).

Before describing these systems, however, it is noted that FIG. 5 also shows packaging 150 containing at least one coiled-up delivery guide 102 and any incorporated guidewire elements. Packaging may include one or more of an outer box 152 and one or more inner trays 154, 156 with peel-away coverings as is customary in medical device product packaging. Naturally, instructions for use 158 may also be provided. Such instructions may be printed product included within packaging 150 or be provided in connection with another readable (including computer-readable) medium. The instructions may include provision for basic operation of the subject devices and associated methodology.

In support of implant delivery, it is also to be understood that various radiopaque markers or features may be employed in the delivery system to 1) locate stent position and length, 2) indicate device actuation and stent delivery and/or 3) locate the distal end of the delivery guide. As such, platinum (or other radiopaque material) bands, use of such material in constructing various elements of the subject systems, and/or markers (such as tantalum plugs) may be incorporated into the system.

Delivery systems according to the present invention are advantageously sized for receipt of existing commercially available guidewires. In the most compact variations, the delivery guide may be adapted to pass over an 0.010 (0.25 mm), 0.014 inch (0.36 mm) or 0.018 inch (0.46 mm) guidewire. The system may even be advantageously practiced with 0.022 inch (0.56 mm) or 0.025 inch (0.64 mm) size guide wires. Of course, intermediate sized wires may be employed as well, especially for full-custom systems. However, one advantage of the delivery guides taught herein (as stated above) is the ease in which they are used in an OTW approach with off-the-shelf hardware. Irregardless of the size selected, features of the invention allow for the size of the delivery system to be minimized relative to the wire size.

In smaller sizes, the system is applicable in "small vessel" cases or applications (where the vessel to be treated has a diameter up to about 3.0 mm). In such systems adapted to receive an 0.010 or 0.014 wire, the inner diameter (ID) of the catheter lumen restraining the stent may be as little as between about 0.014 or 0.018 and about 0.017 or 0.021 inches, respectively. For use with a 0.018 system with adequate room to accommodate a stent and lumen within the stent to pass a guidewire, the catheter lumen ID may be as little as between about 0.022 and 0.025 inches. In any case, the wall thickness of the catheter sleeve holding the stent may advantageously range from about 0.00075 to about 0.0025 inches. Thus, the outer diameter (OD of the catheter body or sleeve/sheath) may advantageously be between about 0.014 and about 0.028 inches (about 1 to about 2 Fr) for use in small vessel applications. The overall OD of the system will depend on (among other things) whether or not balloon features are added or carried by such an integrated system.

In larger sizes, the system is most applicable to larger, peripheral vessel applications, biliary ducts or other hollow body organs. Such applications involve a stent being emplaced in a region having a diameter from about 3.5 to 13 mm (0.5 inch). In which case, a 0.035 to 0.039 inch (about 3 FR) diameter crossing profile system is advantageously provided in which the stent expands (unconstrained) to a size between about roughly 0.5 mm and about 1.0 mm greater than the vessel or hollow body organ to be treated. Sufficient stent expansion is easily achieved with prostheses employing either of the exemplary stent patterns shown in FIGS. 2A/2B or 2C/2D.

Delivery Guide Implant Retention and Release Features

While FIG. 5 illustrates a full-size delivery system, a number of the following figures illustrate detail views of the far or distal end 108 of such a system. The device features are typically incorporated into complete systems and may be used in the manner described, as well as others as may be apparent to those with skill in the art.

Accordingly, FIG. 6A offers a cross-section view of a variation of a working end of a delivery system 160. As shown, system 160 includes delivery guide member 164 having a catheter 162 housing pusher 166, stent 82 having a lumen 168, and elongate member 176 (in this case a mandrel) located within a lumen 170 of catheter 162. As discussed above, without mandrel 176 in place, compression of stent 82 to fit within lumen 170 causes crown and end portions of stent 82 collapse further inward. Such displacement makes it difficult for guidewire 178 to enter stent 82 in order to advance the delivery guide over the same to reach the treatment site. To keep the ends of stent 82 in an open position elongate member or mandrel 176 is located at least partially in stent 82. Thus, as guidewire 178 enters the lumen of stent 82, it displaces elongate member 176 from the stent.

Although mandrel 176 is illustrated as extending through the length of stent 82, variations of the invention include mandrels of varying lengths (i.e., shorter or longer in length than the stent or even the overall length of the delivery system).

System 160 in FIG. 6A is a variation in which mandrel 176 is placed just proximal of the end of catheter 180. This configuration allows for easier entry of the guidewire within the stent lumen 168 at a pocket 180.

To deploy the stent in this variation of the invention, tubular pusher or blocker 166 is used to stabilize the axial position of the stent while the catheter body 162 is withdrawn. This action may be undertaken with or without the guidewire core 178 in place.

Although the system 160 illustrates catheter 162 as having inflation lumen 174 within the catheter body and fluidly coupled to balloon 172 on the catheter body surface, it is noted that variations of the invention includes simple catheters or sheaths. In which case, catheter 162 will not include a balloon.

Figure 6B:
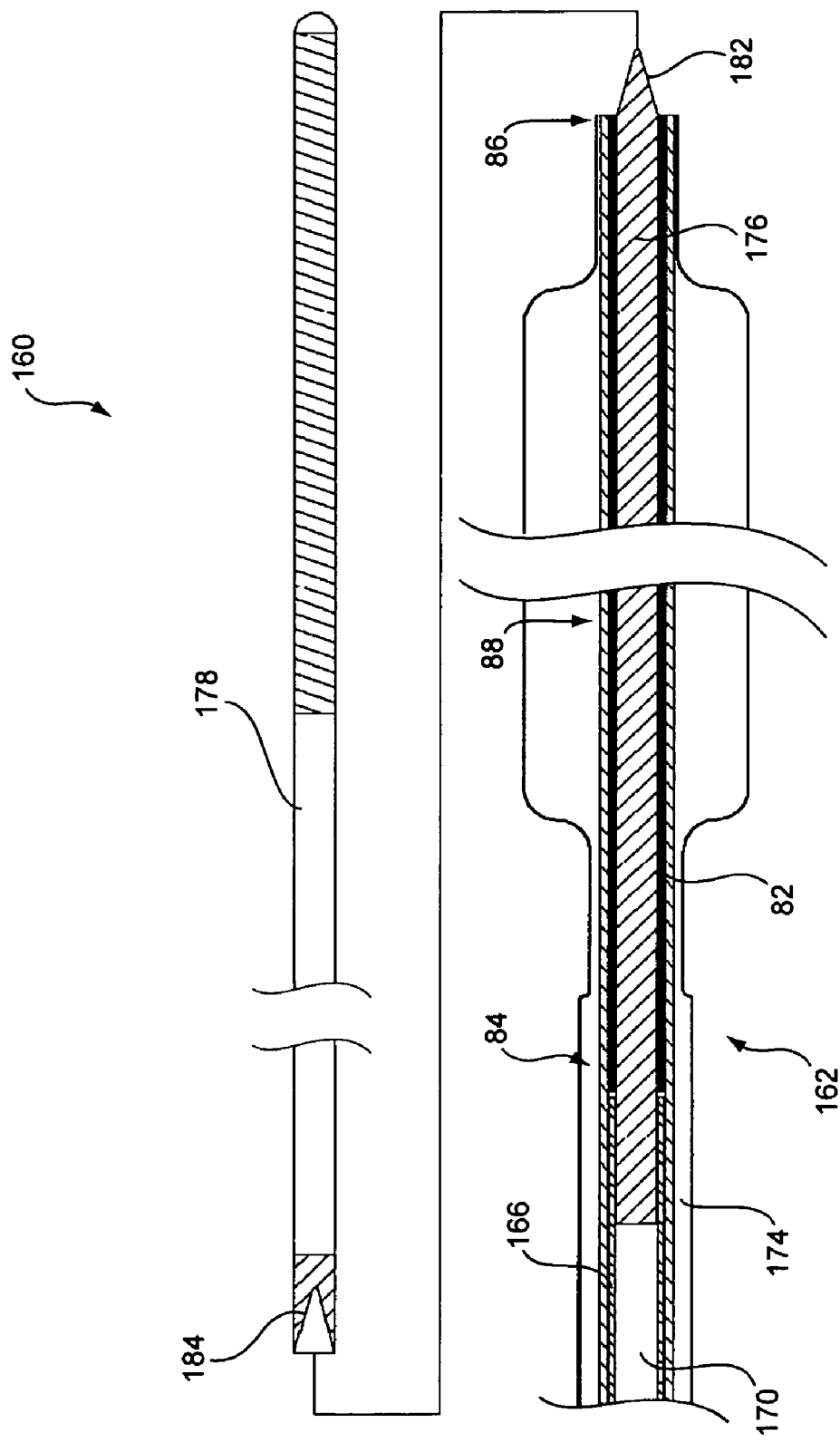

FIG. 6B illustrates another variation of the present invention. In this variation, delivery system 160 includes mandrel 176 having a length slightly greater than that of stent 82. The far end of mandrel 176 extends out of the far end 180 of catheter 162 and is configured with a tapered section 182 to assist in centering or aligning a complimentary recess 184 in guidewire 178. Configured in this manner or otherwise, coupling the guidewire with the mandrel is simplified. Once mated, the delivery catheter is advanced over the guidewire, pushing the mandrel out of the catheter lumen 170 during advancement of the balloon and/or stent alone to the treatment site.

Figure 7:
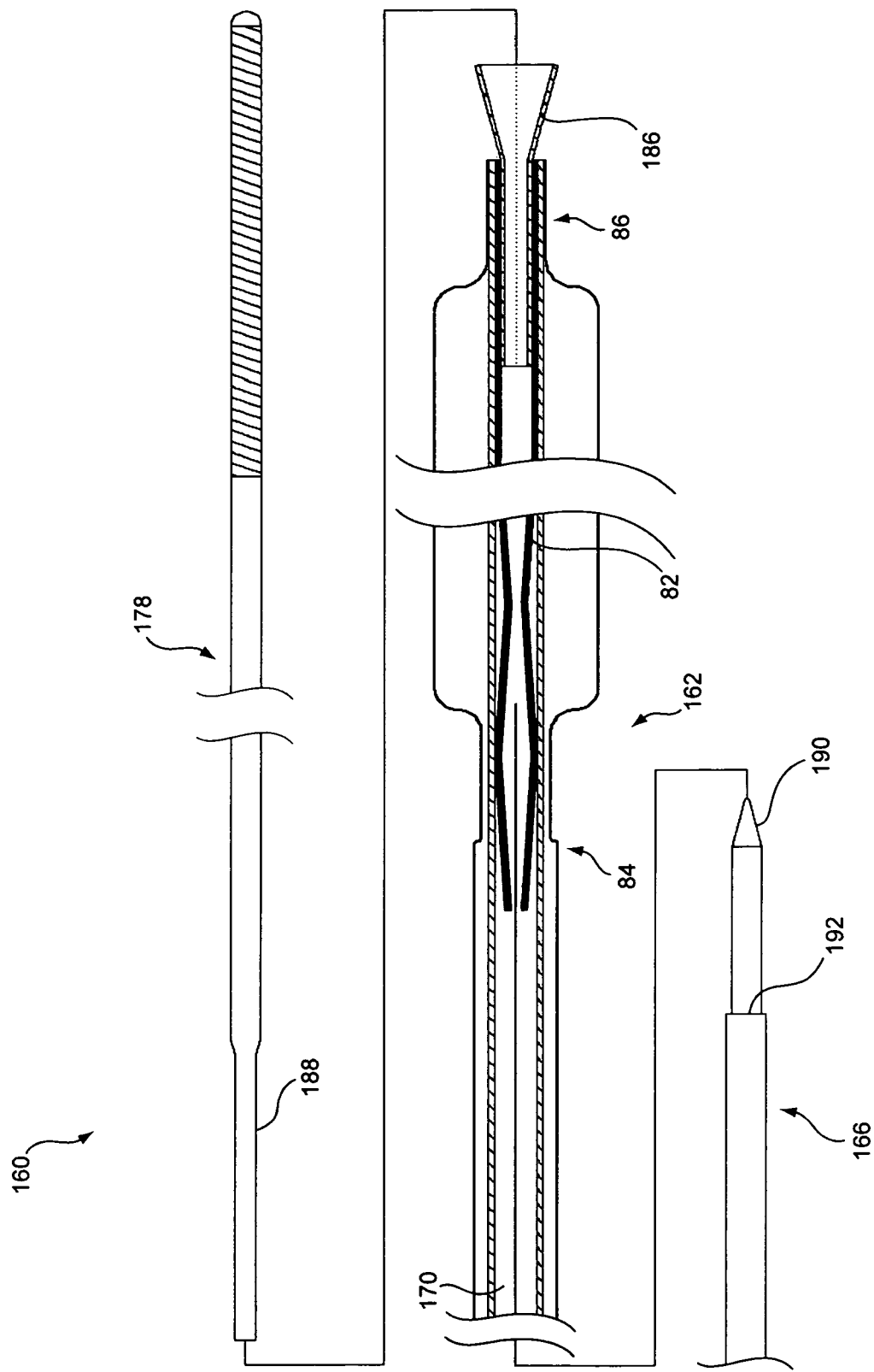
FIG. 7 is a partial cross-sectional view with a distal end of the stent wedged open by an introducer.

FIG. 7 illustrates another variation of the subject intention. As shown, the system 160 includes guidewire 178, balloon catheter 162, pusher 166 with stent 82 placed within balloon catheter. To better fit within an introducer 186 wedging open the far end 86 of stent 82, the near end of guide wire 178 includes a reduced diameter section 188. The introducer may be tearable or pre-split to assist in its removal after receipt of guidewire 178. Introducer 178 will generally have a wide mouth section to assist in directing guidewire into catheter 162.

In use, the medical practitioner advances stepped-down section 188 into the distal end of tearable sheath 186 then through stent 82. Once guidewire 178 is within stent 82, the practitioner removes the introducer. To deliver the stent in this variation of the invention, once the delivery catheter is advanced to the treatment site, the guidewire is removed. It is exchanged for pusher 166. Because nothing is provided to hold open near end 84 of stent 82, it is at least partially closed as illustrated. A blunt-faced pusher may simply abut the end features so-positioned.

However, it is desirable to deliver the stent with a body underlying its near end. The reason is that by providing a body under the struts, the angle that the members can assume during sheath withdrawal are limited, thereby alleviating problematic stent "jumping" at final deployment. To facilitate advancing a portion of pusher 166 within the stent lumen 178 from its proximal side, the tip 190 of pusher 166 is tapered or pointed in order to push through and open the near end 84 of the stent 82. Location of the tip to effect such introduction is guided by the inner lumen 170 of the catheter body. Upon further advancement, a shoulder section 192 of pusher 166 will abut the stent in order prevent its rearward movement while catheter 162 is withdrawn, thereby allowing the stent to expand.

FIG. 8A shows another variation of the inventive system. In this example, delivery system 160 includes catheter 162 housing stent 82 and an internal slider 194. The slider offers a floating blocker interface in contact with near end 84 of stent. By way of an undercut/angled lip 196, keyed ways to interface with complementary sections of the stent (not shown), or otherwise, slider 194 maintains the near end 84 of the stent in an open configuration for introduction of a distal extension 200 of pusher 166. Again, this end of the pusher may underlie the stent to assist with accurate stent placement through avoiding stent jumping. Otherwise, end 200 may be shorter to simply radially interlock with slider 194 or be altogether eliminated. In any case, the pusher is advanced to point within the lumen 170 of the catheter until shoulder 192 abuts slider 194 to stabilize that feature (which—in turn—stabilizes the stent for delivery during withdrawal of the catheter body/sheath).

Another aspect of the variation of the invention shown in FIG. 8A is better illustrated in the end view in FIG. 8B. Here, end wedge features 202 that contact one another to provide an opening 204. A tapered end 206 of guidewire 178 fits easily within such structure. The wedge features on the stent 82 may be "T-shaped" as illustrated, J-shaped, L-shaped, etc.). As shown in FIG. 8C, they may advantageously comprise (e.g., soldered-on tantalum) markers to assist in visualizing stent placement.

However configured, such features may be provided at either end of the stent to prevent end closure. At the distal end, such features facilitate backloaded guidewire entry; at the proximal end, the features facilitate pusher entry into the stent.

Another aspect of the invention illustrated in FIG. 8A concerns the relative placement of the stent and balloon. As shown in FIG. 8A, the stent and/or any slider features may be pushed forward of the balloon 172. In this manner, the thickness or number of layers of material in each region along the axis of the delivery catheter is minimize to promote consistent and/or maximize overall or average system flexibility (especially at the distal end). In like manner, it is also contemplated that the internal feature (stent, slider) may be set proximal to the balloon. However, such a system would require advancement of the balloon past the site of the lesion in order to properly locate the stent for delivery. Because the deflated balloon may not return to an adequately small size, it may be preferred not to push it past the lesion across plaque that could be dislodged.

FIG. 9 shows yet another variation of the invention. It largely differs in principle from the previous examples from the perspective that guidewire 178 need not be introduced into the stent or catheter lumen during a medical procedure. Rather, the delivery catheter 162 is pre-assembled or pre-mounted upon the guidewire to offer an overall system 160 to be used to access a treatment site.

The delivery catheter/balloon catheter 162 is preferably mounted at or near the proximal end of the guidewire 178. A removable torquer 212 set in front of the delivery catheter may be may be used (even pre-mounted to) to manipulate the wire for advancement to a treatment site.

The wire may be a custom or commercially available "exchange-length" wire. With a guidewire 178 that is at least twice the length of catheter 162, the distal length of the wire is fully available for use in navigating to a treatment site. Also, with a wire of such length, the proximal end of the wire will be exposed to allow setting a lock (e.g., another torquer—not shown) to stabilize the axial position of the delivery guide or simply provide sufficient length so that a medical practitioner may grasp the guidewire at the near end of the catheter when the guidewire end has reached the treatment site.

In use, after the distal end of the guidewire is used to reach the target site, the torquer (if used) is removed. Then, the delivery catheter is simply advanced over the wire as in the method described above. To effect stent release, the delivery guide may include a tubular pusher 166 as shown. Otherwise, the guidewire (which originally served as a mandrel to hold open the stent) can be exchanged for a pusher such as that shown in FIG. 7.

FIG. 10 illustrates another variation of the invention. In this variation elongate mandrel member 176 includes a receptacle section 208 for coupling or mating a portion of a guidewire. Such structure may be provided by a commercially available guidewire "extension". FIG. 10 also shows a variation of guidewire 178 including a zigzag or undulating docking portion 210 at the proximal end of guidewire 178.

In practice, the medical practitioner may advance guidewire 178 to the intended site. Subsequently, the practitioner inserts undulating portion 210 of guidewire 178 into receptacle 208 (that may be set within catheter lumen 170 as shown, or advanced beyond this point). Once coupled, delivery catheter is advanced over the primary or lead wire 178 to the treatment site. Otherwise, the guidewire and extension can be employed as is typical, and as further described in the above-referenced patent to Taylor et al. describing such structure.

Figure 11:
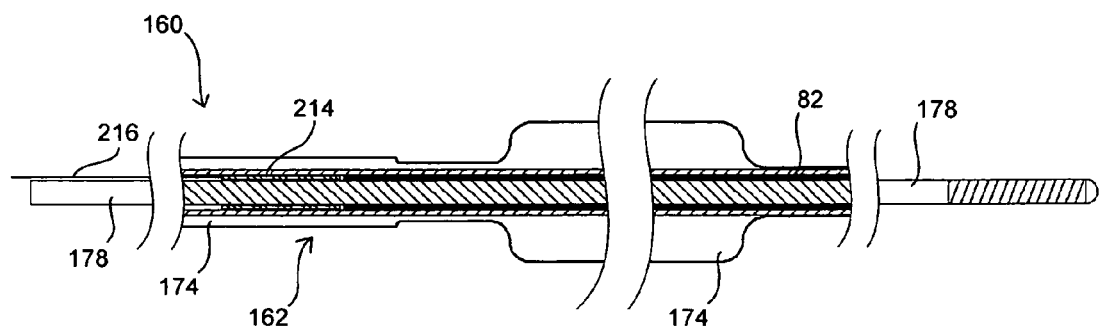
FIG. 11 is a partial cross-sectional view of a variation of the invention where the mandrel/guidewire may be converted to a pusher for delivering the stent.

In another variation of the invention in which guidewire 178 is pre-mounted within stent 82, the system may be "converted" to allow the guidewire to function as a pusher or blocker device. FIG. 11 illustrates such a case. As shown, blocker or pusher section 214 may be a collar or ring placed about guidewire 178 (or elongate member 176). To effect stent release, the medical practitioner may lock pusher/blocker 214 about guidewire 178 (or elongate member 176) to maintain stent 82 in position. Then, the stent is deployed with guidewire 178 and pusher section 214 maintained in a stationary position while the catheter body 162 withdrawn. In such a variation, the pusher may be actuated hydraulically, mechanically (e.g., by pulling a pin wedging open a spring-loaded body) or via a shape memory alloy recovery upon heating (e.g., by passing electrical current therethrough, or warm saline across the body) to clamp the pusher onto or with a groove in the guidewire. In either of the latter instances, a wire 216 (for carrying current or transmitting force) may be provided to effect the desired actuation.

Figure 12:
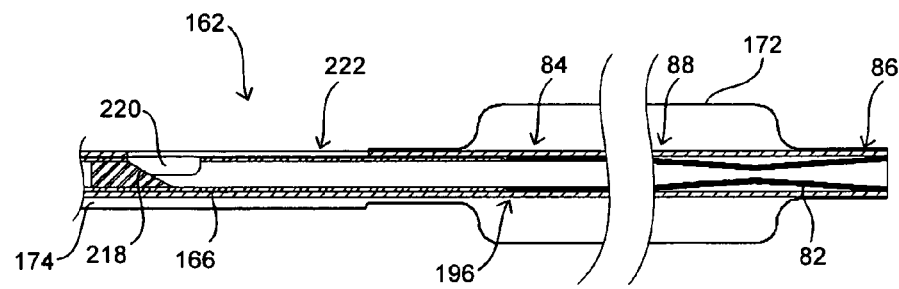
FIG. 12 is a partial cross-sectional view of a rapid-exchange variation of the present invention.

FIG. 12 shows yet another variation according to the present invention. In this variation, delivery catheter 162 is configured as a rapid-exchange (RX) system and will therefore enjoy such associated benefits. To facilitate backfeeding a guidewire within the device, the distal ends 86 of the stent may be held open in the manner described in connection with FIGS. 8A-8C. A different approach—especially another one as described herein—could be used instead. Though not necessary, the proximal end of the stent may also be held open by undercut features 196. When no features are provided to hold the proximal end 84 of the stent open, it will typically be deployed with the guidewire in place in order to align the stent near end and pusher 166 far end.

As such, the RX system pictured offers many of the features of the OTW systems described above. The RX system differs primarily in that pusher 166 includes a ramp 218 and opening 220 so that it can pass a guidewire through its side (generally near a distal end of the system). The ramp may be provided by a plug set within the lumen of the pusher as shown, by a formed section of the pusher hypotube, by a welded-in septum or otherwise. Further, the catheter body may include a slot 222 providing clearance for an internal guidewire during withdrawal of the catheter body to release the stent while stabilizing the pusher. For systems in which the wire is to be removed prior to stent delivery, a simple hole or aperture in lieu of slot 222 will suffice.

Of course, the delivery system in FIG. 12 may be configured with or without a balloon—as may the others inventive systems described herein. Furthermore, alternate RX configurations may be employed. For instance, a separate RX lumen originating at the catheter wall could be provided and merge with lumen 170 of pusher 166. Other options are possible as well. Yet, the RX variation of the invention shown may be preferred from the perspective of simplicity and/or minimal overall system diameter.

Figure 13:
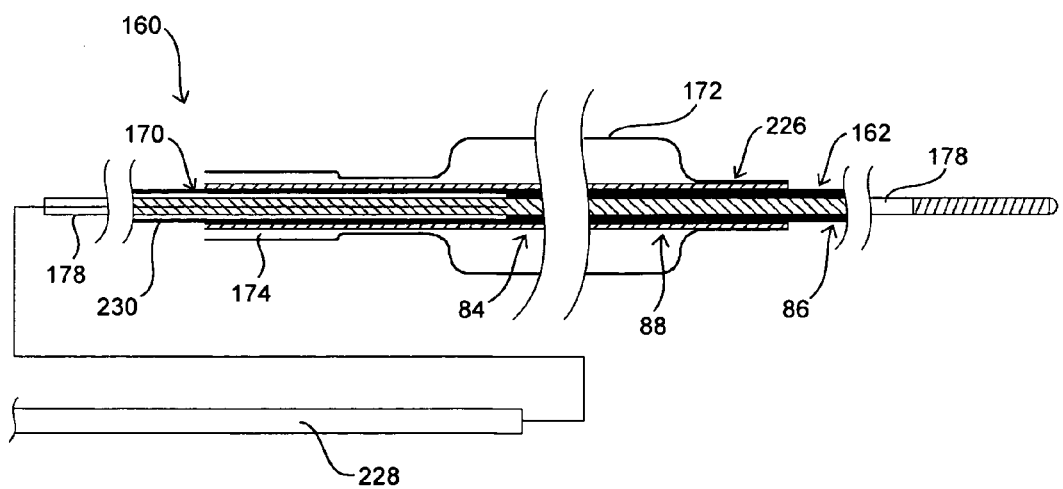
FIG. 13 is a final partial cross-sectional view of a variation of the present invention in which the delivery system is sized for use within such a balloon catheter body as optionally employed in other variations of the invention.

Yet another approach exists where the wire is used independently of the balloon catheter. In the variation shown in FIG. 13, the delivery guide 224 is sized for use within such a balloon catheter body 226. In which case, the delivery guide body typically comprises a simple sheath. To minimize sheath outer diameter and still allow for an OTW device, a smaller guidewire 178 (e.g., an 0.010 inch vs. 0.014 inch or larger) is used. Other than such sizing, that allows it to be fit within balloon catheter lumen 170, the core delivery guide of the overall system resembles the features and use of that which is shown in FIG. 9. However, since the system may be smaller, whereas the delivery system in FIG. 9 includes an (optionally) integral tubular pusher/stabilizer 166, delivery system 160 in FIG. 13 includes a pusher rod 228 to exchange for guidewire 178.

As for construction, in that the system comprises a simple sheath, the wall of the sheath may be a hybrid structure, it may comprise hypotube at a proximal end, with a distal polymer restraint connected (typically bonded with epoxy-based glue) there. A cut-out Nitinol tube body such as used in the Synchro™ (Boston Scientific) guidewire may be desirable in this regard. The restraint may advantageously comprise Polyamide tubing, PEEK, another engineering polymer or hybrid construction such as presented in commonly assigned U.S. patent application Ser. No. 11/147,999 entitled, "Ten-thousandths Scale Metal Reinforced Stent Delivery Guide Sheath or Restraint." Indeed any of the techniques or technology described therein may be used in the present application. Accordingly that patent application is incorporated herein by reference in it entirety.

Variations

The invention includes methods that may be performed using the subject devices or by other means. The methods may all comprise the act of providing a suitable device. Such provision may be performed by the end user. In other words, the "providing" (e.g., a delivery system) merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as is generally known or appreciated by those with skill in the art. For example, one with skill in the art will appreciate that a lubricious coating (e.g., hydrophilic polymers such as polyvinylpyrrolidone-based compositions, fluoropolymers such as tetrafluoroethylene, hydrophilic gel or silicones) may be placed on the core member of the device, if desired to facilitate low friction manipulation. The same may hold true with respect to method-based aspects of the invention in terms of additional acts as commonly or logically employed.

In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. Reference to a singular item, includes the possibility that there are a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth n the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language. That being said, we claim:

That being said, we claim:

1. A method for stenting a body passageway, the method comprising:
   locating a distal end of a first guidewire at a site within the body passageway;
   feeding a delivery catheter over the first guidewire, said delivery catheter having a catheter body including a lumen, a compressed superelastic stent slidably compressed in the lumen, and means to maintain at least a far end of the stent in an open configuration when the stent is compressed and in said lumen and prior to insertion of the first guidewire in the stent while feeding the delivery catheter over the first guidewire; said means comprising a mandrel extending through at least a portion of the stent;
   pushing the mandrel from the lumen of the delivery catheter body by feeding the delivery catheter over the first guidewire; and
   deploying the stent by withdrawing the catheter body while the stent position is maintained by a blocker.

2. The method of claim 1, wherein the site is within a coronary artery selected from the group of small diagonals, PDA, and OM vessels.

3. The method of claim 2, wherein a diameter at the site is between about 2 mm and about 3 mm.

4. The method of claim 1, wherein the guidewire has a crossing profile of about 0.014 inches in diameter.

5. The method of claim 1, wherein the delivery catheter includes an angioplasty balloon and an inflation lumen, the method further comprising dilatating the balloon.

6. The method of claim 1, wherein the mandrel extends through the length of the catheter body.

7. The method of claim 1, wherein the mandrel is a second guidewire.

8. The method of claim 1, wherein the mandrel comprises an extension wire including a distal end adapted to dock with the first guidewire.

9. The method of claim 1, wherein the blocker comprises an end of an elongate member actuatable from a proximal end of the delivery catheter.

10. The method of claim 9, wherein the elongate member is tubular and the guidewire remains in the delivery guide lumen during stent delivery.

11. The method of claim 1, wherein the delivery catheter is fed in an over-the wire fashion.

12. The method of claim 1, wherein the guidewire has a crossing profile of about 0.010 inches in diameter.

13. The method of claim 1, wherein said superelastic stent directly contacts the guidewire and is slidable thereover.

* * * * *